United States Patent [19]

Hayano et al.

[11] Patent Number: 5,284,762
[45] Date of Patent: Feb. 8, 1994

[54] PEPTIDYL PROLYL-CIS.TRANS-ISOMERASE

[75] Inventors: Toshiya Hayano; Setsuko Katou; Noboru Maki; Nobuhiro Takahashi; Masanori Suzuki, all of Iruma, Japan

[73] Assignee: Tonen Corporation, Tokyo, Japan

[21] Appl. No.: 555,944

[22] Filed: Jul. 19, 1990

[30] Foreign Application Priority Data

Jul. 19, 1989 [JP] Japan ................... 1-184738
Oct. 6, 1989 [JP] Japan ................... 1-260244
Dec. 29, 1989 [JP] Japan ................... 1-344705

[51] Int. Cl.$^5$ ............ C12N 9/90; C12N 15/61; C12N 15/70
[52] U.S. Cl. ............. 435/233; 435/252.31; 435/320.1; 536/23.2
[58] Field of Search ............ 435/69.1, 172.3, 252.3, 435/252.33, 322.1, 233; 536/27, 23.2

[56] References Cited

U.S. PATENT DOCUMENTS 5,109,112 4/1992 Siekierka et al. ............ 530/350

OTHER PUBLICATIONS

Lang, K., et al., 1988, *Nature*, 331: 453-455.
Fischer, G., et al., 1989, *Nature*, 337: 476-478.
B. Haendler et al., Gene, vol. 83, No. 1, pp. 39-46, 1989.
Proceedings of the Nat'l. Academy of Sciences 87, pp. 4028-4032 (1990) Liu, J et al., "Peptidyl-probyl cis-trans-isomerase . . . ".
A. J. Koletsky et al., J. Immunol. 137, 1054-1059, 1986.
M. Tropschug et al., J. Biolog. Biochem. vol. 263, No. 28, 14433-14440, 1988.
S. Schneowly et al., Proc. Natl. Acad. Sci. USA, 86, 5390-5394, 1989.
Bih-Hwa Shieh et al., Nature, 338, 67-70, 1989.
N. Takahashi et al., Nature, 337, 474-475, 1989.
K. Lang et al., Nature, 329, 268-270, 1987.
G. Fischer et al., Biomed. Biochim. Acta 43, 1101-1111, 1984.
G. Fischer et al., Nature, 337, 476-478, 1989.

*Primary Examiner*—Robert A. Wax
*Assistant Examiner*—William W. Moore
*Attorney, Agent, or Firm*—Michael N. Meller

[57] ABSTRACT

A yeast PPIase characterized by possessing the following properties: (1) acting on and isomerizing the bond $X_{aa}$-Pro (wherein $X_{aa}$ stands for any amino acid and Pro stands for L-proline), (2) exhibiting a single molecular weight of about 17,000 daltons in the sodium dodecyl sulfate-polyacrylamide concentration gradient gel electrophoresis, (3) exhibiting a single isoelectric point of about 6.2 in the isoelectric focusing, and (4) inhibited by CsA;

an *E. coli* PPIase-$\beta$ characterized by possessing the following properties: (1) acting on and isomerizing the bond $X_{aa}$-Pro (wherein $X_{aa}$ stands for any amino acid and Pro for L-proline), (2) exhibiting a single molecular weight of about 20,000 daltons in the sodium dodecyl sulfate-polyacrylamide concentration gradient gel electrophoresis, (3) exhibiting a single isoelectric point of about 5.0 in the isoelectric focusing, and (4) no being inhibited by CsA;

an *E. coli* PPIase-$\alpha$ characterized by possessing the following properties: (1) acting on and isomerizing the bond $X_{aa}$-Pro (wherein $X_{aa}$ stands for any amino acid and Pro for L-proline), (2) exhibiting a single molecular weight of about 22,000 daltons in the sodium dodecyl sulfate-polyacrylamide concentration gradient gel electrophoresis, (3) exhibiting a single isoelectric point of about 9.7 in the isoelectric focusing, and (4) not being inhibited by CsA.

6 Claims, 30 Drawing Sheets

☆ POSITION OF CYSTEIN RESIDUE
▨ HIGH HOMOLOGY REGION

1. MOLECULAR WEIGHT STANDARDS
2. PPIase 1. pI STANDARDS
2. PPIase

Fig. 6

```
                    Val Ser Phe Glu Leu Phe Ala Asp Lys Val Pro Lys Thr Ala Glu Asn Phe Arg Ala Leu
GAATTCCG            GTC TCC TTC GAG CTG TTT GCA GAC AAA GTT CCA AAG ACA GCA GAA AAC TTC CGT GCT CTG

Ser Thr Gly Glu Lys Gly Phe Gly Tyr Lys Gly Ser Cys Phe His Arg Ile Ile Pro Gly Phe Met Cys
AGC ACT GGG GAG AAA GGA TTT GGT TAT AAA GGT TCC TGC TTT CAC AGA ATA ATT CCA GGA TTT ATG TGC

Gln Gly Gly Asp Phe Thr Arg His Asn Gly Thr Gly Lys Ser Ile Tyr Gly Lys Phe Asp Asp
CAG GGT GGT GAC TTC ACA CGC CAT AAT GGC ACT GGT AAG TCC ATC TAT GGA AAA TTT GAT GAT

Glu Asn Phe Ile Leu Lys His Thr Gly Pro Gly Ile Leu Ser Met Ala Asn Ala Gly Pro Asn Thr Asn
GAG AAT TTT ATC CTG AAG CAT ACG GGT CCT GGC ATC TTG TCC ATG GCA AAT GCT GGC CCC AAC ACA AAC

Gly Ser Gln Phe Phe Ile Cys Thr Ala Lys Thr Glu Trp Leu Asp Gly Lys His Val Val Phe Gly Lys
GGT TCC CAG TTT TTC ATT TGC ACT GCC AAG ACT GAG TGG TTG GAT GGC AAA CAT GTG GTC TTT GGC AAA

Val Lys Glu Gly Met Asn Ile Val Glu Ala Met Glu Arg Phe Gly Ser Arg Asn Gly Lys Thr Ser Lys
GTG AAA GAG GGC ATG AAT ATT GTG GAA GCC ATG GAG CGC TTT GGG TCC AGG AAT GGC AAG ACC AGC AAG

Lys Ile Thr Ile Ala Asp Cys Gly Gln Ile
AAG ATC ACC ATT GCT GAC TGT GGA CAA ATC   TAATAAATTTGACTTGTTTTATCTTAACCATCAGACCATTCCTTCTGTAGC

TCAGGAGAGCACCCCTTTACCCCCACCTGCTTGAAATAGCCCATAATCTCTGTGCTCTCACTGCAG
```

Fig. 7-1

```
TTCCCTGTATAAATATAAACGTATTCTCTTGAGCCTTCTATCCTTTTGGCCACTGTCGTCATCATTGTTCCTCCTTTTCGCTAGATA
                                                                         Met Ser Gln Val Tyr Phe
GGTTATATTAAGATTTGTCTTGAATTTAATATCTCAACTCAATCCAAACTCAACCGCTAATACTACC ATG TCC CAA GTC TAT TTT

Asp Val Glu Ala Asp Gly Gln Pro Ile Gly Arg Val Val Phe Lys Leu Tyr Asn Asp Ile Val Pro Lys
GAT GTC GAA GCT GAT GGC CAA CCA ATT GGC CGT GTC GTT TTC AAG TTG TAC AAC GAC ATA GTC CCA AAG
        PstI
Thr Ala Glu Phe Arg Ala Leu Cys Thr Gly Glu Lys Gly Phe Gly Tyr Ala Gly Ser Pro Phe His
ACT GCA GAA TTC AGA GCT CTA TGT ACC GGT GAA AAG GGA TTC GGC TAC GCT GGC TCT CCA TTC CAC
                                                                              KpnI
Arg Val Ile Pro Asp Phe Met Leu Gln Gly Gly Asp Phe Thr Ala Gly Asn Gly Thr Gly Gly Lys Ser
AGA GTT ATT CCA GAC TTC ATG TTG CAA GGT GGT GAT TTC ACT GCT GGT AAC GGT ACC GGC GGT AAG TCT
                                                                                      NcoI
Ile Tyr Gly Gly Lys Phe Pro Asp Glu Asn Phe Lys Lys His His Asp Arg Pro Gly Leu Leu Ser Met
ATC TAC GGT GGC AAA TTC CCA GAT GAA AAC TTC AAG AAG CAC CAC GAC AGA CCA GGT TTG TTG TCC ATG
                                                                NcoI
Ala Asn Ala Gly Pro Asn Thr Asn Gly Ser Gln Phe Ile Thr Thr Val Pro Cys Trp Leu Asp
GCC AAC GCC GGT CCA AAC ACC AAC GGT TCT CAA TTC ATC ACC ACC GTT CCA TGC TGG TTG GAC

Gly Lys His Val Val Phe Gly Glu Val Val Asp Gly Tyr Asp Ile Val Lys Lys Val Glu Ser Leu Gly
GGT AAG CAT GTT GTT TTT GGT GAA GTT GTT GAC GGT TAC GAC ATC GTT AAG AAG GTT GAG TCC TTG GGT
```

Fig. 7-2

```
Ser Pro Ser Gly Ala Thr Lys Ala Arg Ile Val Val Ala Lys Ser Gly Glu Leu  stop
TCT CCT TCC GGT GCC ACC AAG GCT AGA ATT GTT GTT GCC AAG TCC GGT GAA TTA TAA CCCGTCTGCCTGGAA
                                                                                         *

CAATACAGCAAAAATTGAAACGAACTATTCTCTCTTAAATTATATGTATAAGGTATGTGTATGTATGACAATCAATTCTTATAAC

TAACTCTTCCTACCTATATCGGAGTATGTTGCCAGGCTTGCCAACTAGCCAACTACCGCCTAGTTATGCCTGTTAAGTTGACGCCGCCGG
KpnI
GTACC
```

—○— PPIase ACTIVITY
——— $A_{280}$

PPIase-α

PPIase-β

FIG.15a
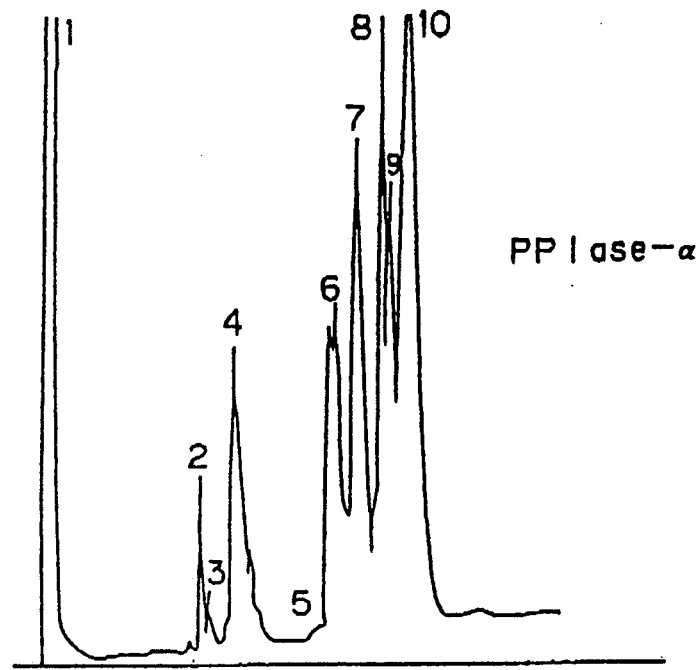
PPIase-α
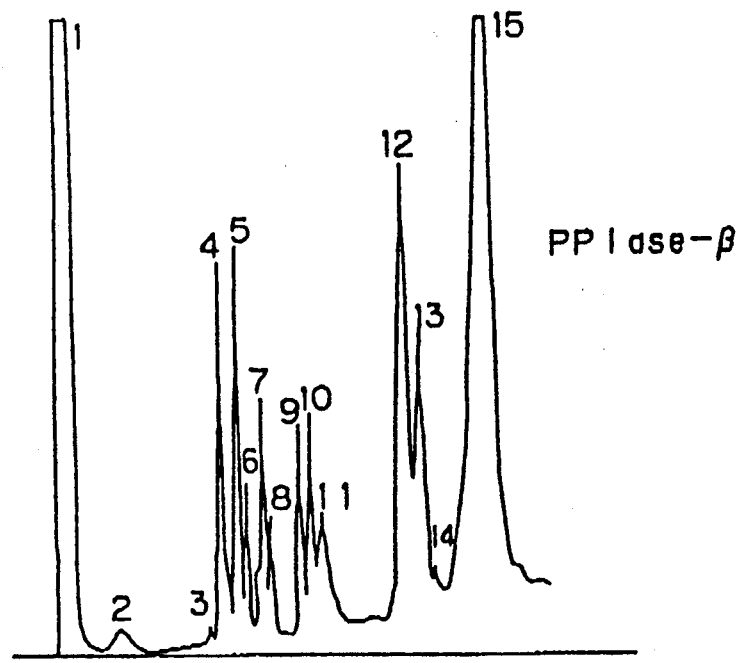
PPIase-β
FIG.15b

Fig.17-1

```
HindIII
A AGCTTTCGCCATTTCATTGGCGCGTTTGATGATTTTGTCGTCGATATGTTGCGCACATACTTCAGTTTATAGCCGAGGAAA
       EcoRV
CGCAGATAGCGCGCAACCACGTCAAAAGCAACAAAGTACGCCCGTGACCGATATGACAGAGATCGTAAACGGTGATTCCACACACGTACA
TGCCGACTTCCCCGGCGTGAATAGGCTTAAATTCCTCTTTTGGCGTGTCAGAGTATTGAAGATTTTAGCATGAAGATTCCGTTTAGGA
                                                                          PvuI
CATGTGTGGGTAATTGAGTTGCGTATAATACCCATATTCCCGCCGAATCAGCATACATTGCGTGATGATCCGATCGTGCGGTTATGCTA Met Val Thr Phe His Thr Asn
TAACACCACCCTATATATGACCCGAACTGGGTTGAAGCACCATCAACGGAACAGGATGCAAAA ATG GTT ACT TTC CAC ACC AAT His Gly Asp Ile Val Lys Thr Phe Asp Asp Lys Ala Pro Glu Thr Val Lys Asn Phe Leu Asp Tyr
CAC GGC GAT ATT GTC AAA ACT TTT GAC GAT AAA GCA CCT GAA ACA GTT AAA AAC TTC CTG GAC TAC Cys Arg Glu Gly Phe Tyr Asn Asn Thr Ile Phe His Arg Val Ile Asn Gly Phe Met Ile Gln Gly Gly
TGC CGC GAA GGT TTT TAC AAC AAC ACC ATT TTC CAC CGT GTT ATC AAC GGC TTT ATG ATT CAG GGC GGC Gly Phe Glu Pro Gly Met Lys Gln Lys Ala Thr Lys Glu Pro Ile Lys Asn Glu Ala Asn Asn Gly Leu
GGT TTT GAA CCG GGC ATG AAA CAA AAA GCC ACC AAA GAA CCG ATC AAA AAC GAA GCC AAC AAC GGC CTG Lys Asn Thr Arg Gly Thr Leu Ala Met Ala Arg Thr Gln Ala Pro His Ser Ala Thr Ala Gln Phe Phe
AAA AAT ACC CGT GGT ACG CTG GCA ATG GCA CGT ACT CAG GCT CCG CAC TCT GCA ACT GCA CAG TTC TTC Ile Asn Val Val Asp Asn Asp Phe Leu Asn Phe Ser Gly Glu Ser Leu Gln Gly Trp Gly Tyr Cys Val
ATC AAC GTG GTT GAT AAC GAC TTC CTG AAC TTC TCT GGC GAA AGC CTG CAA GGT TGG GGC TAC TGC GTG Phe Ala Glu Val Val Asp Gly Met Asp Lys Val Asp Lys Ile Lys Gly Val Ala Thr Gly Arg Ser Gly
TTT GCT GAA GTG GTT GAC GGC ATG GAC AAA ATC AAA GGT GTT GCA ACC GGT CGT AGC GGT
```

Fig. 17-2

```
     Met His Gln Asp Val Pro Lys Glu Asp Val Ile Ile Glu Ser Val Thr Val Ser Glu   *
     ATG CAC CAG GAC GTG CCA AAA GAA GAC GTT ATC ATT GAA AGC GTG ACC GTT AGC GAG TAA TCGTGGCGACA
            BglII
     CTCTTTATTGCAGATCT
```

Fig. 18
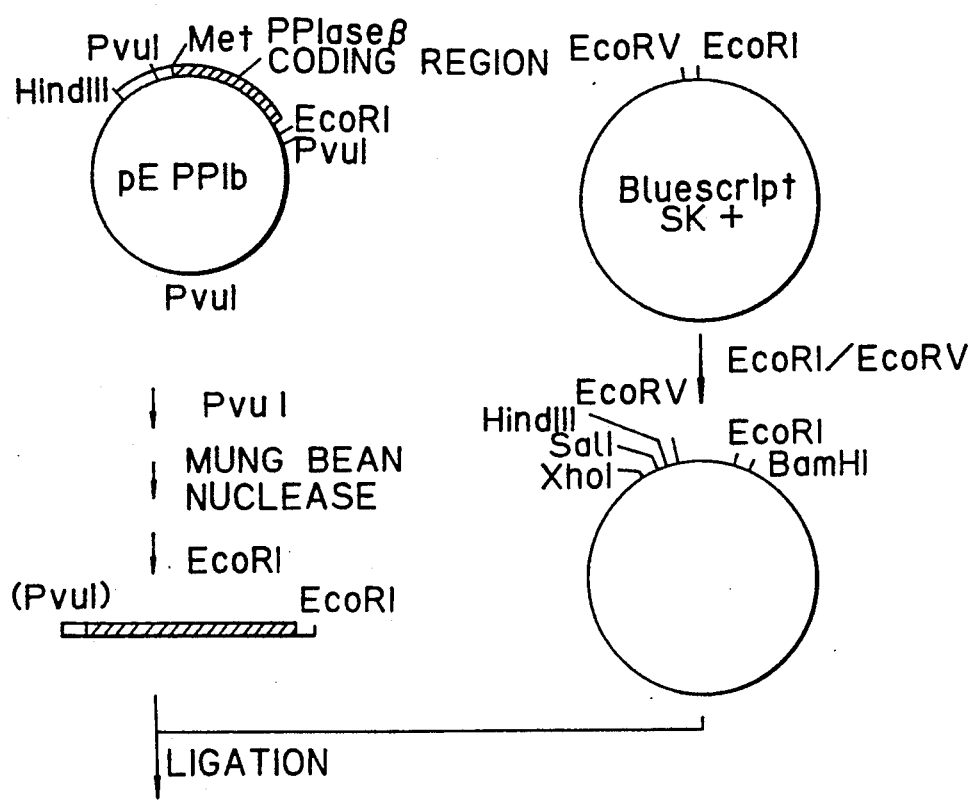
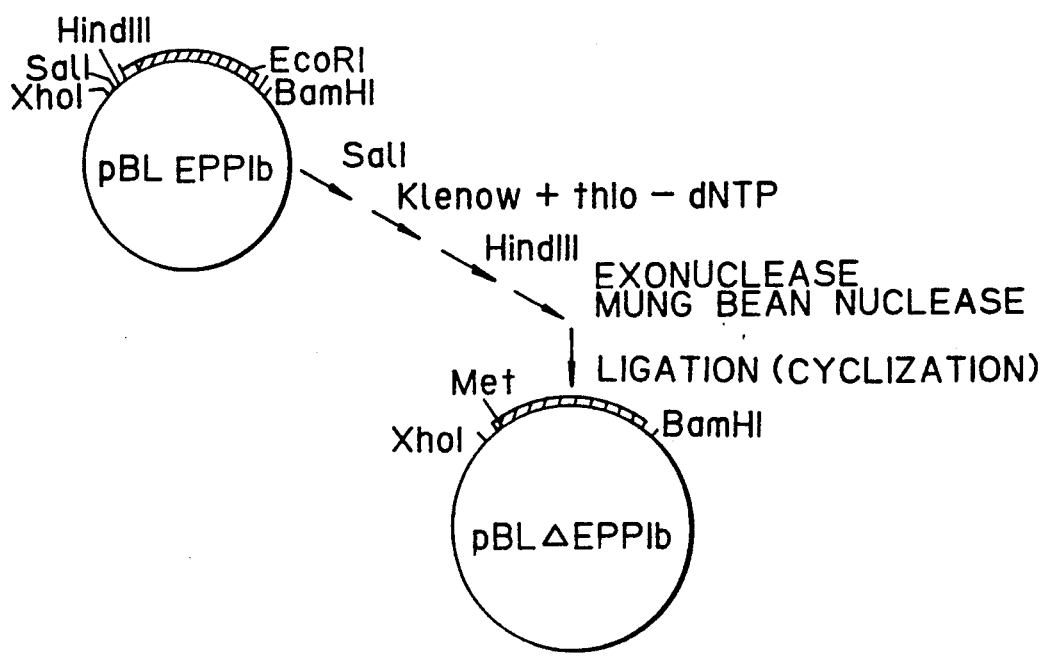

```
     trpE                         PPIaseβ GENE
   PROMOTER                      INITIATION CODEN
                                      Met
--- A T C G T C G A G G T C G C A A A A A T G ---
--- T A G C A G C T C C A G C G T T T T T A C ---
```

LANE
1. MOLECULAR WEIGHT STANDARDS
2. E.coli HB101 SOLUBLE FRACTION
3. TRANSFORMANT SOLUBLE FRACTION
4. E.coli HB101 INSOLUBLE FRACTION
5. TRANSFORMANT SOLUBLE FRACTION LANE 1: NATURAL E.coli PPIase-β
LANE 2: RECOMBINANT E.coli PPIase-β
LANE 3: ISOELECTRIC POINT STANDARDS Fig. 25
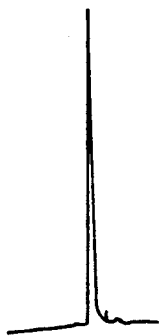
NATURAL TYPE (β)
RECOMBINANT TYPE
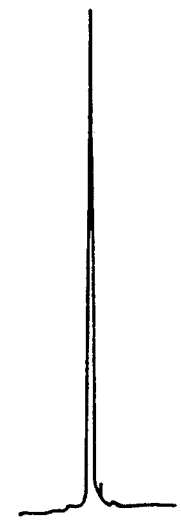
NATURAL TYPE (β)
+
RECOMBINANT TYPE

```
PORCINE     - L S M A N A G - P N T N G S Q F F I C T A K T E - - - - - - - - - - - W L D G K H - V V F G K V -
BOVINE      - L S M A N A G - P N T N G S Q F F I C T A K T E - - - - - - - - - - - W L D G K H - V V F G K V -
HUMAN       - L S M A N A G - P N T N G S Q F F I C T A K T E - - - - - - - - - - - W L D G K H - V V F G K V -
RAT         - L L S M A N A G - P N T N G S Q F F I C T A K T E - - - - - - - - - - - W L D G K H - V V F G K V -
DROSOPHILA  - L G M A N R G - P N T N G C Q F Y I C T V G A K - - - - - - - - - - - W L D G K H - I V F G I V A
N.CRASSA    - L S M A N A G - P D T N G S Q F F I T T V P T S - - - - - - - - - - - W L D G K H - V V F G K V -
YEAST       - L S M A N A G - P N T N G S Q F F I T T V P C P - - - - - - - - - - - W L D G K H - V V F G E V A
E.COLI-β    - L A M A R T Q A P H S A T A Q F F I N V A D N A - - - - - - - - - - - W L D G R H - V V F G E V -
E.COLI-α    - A R T A D K D S X A D Q F F I N V A D N A D F L N P S G E S L Q G W G C V F A E V D G M D E
                                                                                        D F G Y A V F G K M D V

PORCINE     - K E G M N I V E A M E R F G S R N G - - - M T S K K I A D C G Q L* - - -
BOVINE      - K E G M N I V E A M E R F G S R N G - - - M T S K K I A D C G Q L* - - -
HUMAN       - K E G M N I V E A M E R F G S R N G - - - M T S K K I A D C G Q L* - - -
RAT         - K E G M S I V E A M E R F G S R N G - - - M T S K K I A D C G Q L E* - -
DROSOPHILA  - L E G M D T I Y A L E D V K T D T D - - D F P V E I S N C G E I P T E Q F - - -
N.CRASSA    D D E S M K V K A L E A T G S S G A I H R Y S K K I V D C G A L* - - -
YEAST       - V D G Y D I V K V E S L G S P S G - - A T M A R V A K S G E L* - - -
E.COLI-β    - V D M K G V A T G R S G M H Q D V P K E D V I E S V T V S E* -
E.COLI-α    - A D M I S Q V P X H D V G
```

PEPTIDYL PROLYL-CIS.TRANS-ISOMERASE

BACKGROUND OF THE INVENTION

1. Field of the Invention:

The present invention relates to peptidyl prolyl-cis, trans isomerases (pplase) derived from *Escherichia coli* and yeast, methods of producing the same, and genes coding for the same.

The PPIase accelerates a protein folding reaction by catalyzing the isomerization of prolyl peptide bonds in the protein. It is useful as a means for activating an inactive protein produced by genetic engineering and as a reagent for enzymological analysis. Its corresponding gene coding is useful for the production of the enzyme by genetic engineering, and it is also expected to be used as starting material for the gene which allows for the production, by genetic engineering, of the enzyme derivatives in which the enzymatic activity, intracellular localizability, substrate specificity and stability thereof have been altered. The present invention further provides means for efficient production of a useful protein having a correct conformation by expressing the above-mentioned gene in the same cells [as that] in which other gene coding for the useful protein is expressed.

2. Description of the Related Art:

PPIase was found in porcine kidneys (Fisher, G., Bang, H. & Mech, C. *Biomed. Biochim. Acta*, 43, 1101-1111 (1984)], and is known to have the enzymatic activity of isomerizing an $X_{aa}$—Pro bond (wherein $X_{aa}$ stands for any amino acid and Pro for L-proline) [Fisher, G., Bang, H. & Mech, C., *Biomed. Biochim. Acta*, 43, 1101-1111 (1984)] and to accelerate a protein folding reaction in some denaturated proteins such as immunoglobulin L chain and ribonuclease $T_1$ [Lang, K., Schmid, F. & Fisher, G., *Nature*, 329, 263-210 (1987)]. The amino acid sequence of the enzyme purified from porcine kidneys was shown to be identical with that of cyclophilin, a protein known to bind to an immunosuppressive agent, cyclosporine A (CsA) which has been found to inhibit the PPIase activity. Since the immunosuppressive activity is directly proportional to the binding ability of CsA derivatives to cyclophilin, which represents most of the CsA-binding activity in lymphoid cells, it is inferred that the action of CsA, for example, an immunosuppressing action in T-cells is mediated through the inhibition of the PPIase activity [Takanashi, N., Hayano, E. & Suzuki, M., *Nature*, 337. 473-475 (1989)]. The CsA binding and the PPIase activities were found in almost all organs and an nearly all species. However it is not known how CsA acts specifically on the immune system and particularly on T cells, during an organ transplantation, this action has not been explained.

Rhodopsin, a visual pigment occurring in animal retinas, consists of a chromophore, 11-cis-retinal, bonded to opsin in the protein portion of rhodopsin. It is associated with visual transduction in the photoreceptor cells in which the chromophore is gradually converted and the maximum wavelength of absorption is consequently varied under the influence of light. In Drosophila a mutant in which the conversion of the precursor opsin to the rhodopsin is inhibited, is known. The ninaA gene responsible for this inhibition has been isolated and a nucleotide sequence thereof has been determined. As a result, it has been demonstrated that the ninaA gene codes for a ptotein having a homology to cyclophilin in the amino acid sequence. Accordingly, since the ninaA codes for a cyclophilin-like protein and the cyclophilin is identical with the PPIase, the ninaA gene probably encodes a protein possessing a PPIase activity. Thus, its activity is assumed to effect the formation of rhodopsin from its precursor opsin by controlling its folding reactions. The ninaA gene is exclusively expressed in the head part containing photoreceptor cells, and in the other parts of the body, gene fragments hybridizing with the ninaA gene and possessing a different size therefrom are detected. Consequently, it is inferred that the ninaA gene is specifically expressed in the photoreceptor cells and functions only in the formation of rhodopsin [Shieh, B. -H., Stamnes, M. A, Seavello, S., Harris, G. L. & Zuker, C. S., *Nature*, 338, 67-70 (1989); and Schneuwly, S., Shortridge, R. D., Larrivce, D. C., Ono, T., Ozaki, M. & Pak, W. L., *Proc. Natl. Acad. Sci USA.*, 86 (1989)].

Likewise, if a PPIase is specifically expressed in cells the presence of the T-cell specific form may offer an explanation for the specific effect of CsA on the T cells. This assumption is supported by the observation that many gene copies capable of hybridizing with the cyclophilin gene are present in mammalian cells [Haendler, B., Hofer Warbinek, R. & Hofer, E., *EMBO J.*, 6, 547-950 (1987)]. Only one kind of cyclophilin is confirmed to be expressed in each cell to far analyzed, and no multiplicity is found in the protein so expressed. A proof of the presence of several cyclophilins or PPIases in one species may well be theoretically accepted as evidence that each PPIase has a specific protein substrate.

In the case of Neurospora the presence of two species of cyclophilin mRNA transcribed from a single gene is known. One of these mRNAs codes for the cyclophilin molecule present in the cytoplasm, and another mRNA codes for a mitochondrial form having an additional signal sequence for its translocation to mitochondria. The latter protein, after translocation in the mitochondrion, is processed and forms a molecular species identical with the cyclophilin present is the cytoplasm. In this case, therefore, one molecular species of active protein is actually present and the multiplicity is ascribable to a difference in the localization of one protein in the cell [Tropschug, M., Nicholson, D. W., Hartl, F. -U., Köhler, H., Pfanner, N., Wachter, E. & Neupert, W., *J. Biol. Chem.* 263, 14433-14440 (1988)].

The catalytic effect of PPIase on the protein folding was investigated in nine kinds of proteins, i.e., concanavalin A, prothrombin, ribonuclease A, ribonuclease $T_1$, cytochrome C, $\beta$-lactoglobulin, meiokinase, chymotrypsinogen, and pepsinogen, which are known to be such that, during the refolding of the protein from the denatured state to the active state, the isomerization of the prolyl-containing peptide bonds constitutes the rate-determining step in the reconstruction of the denatured protein. However, the refolding of only two kinds of these proteins, i.e., ribonuclease T and cytochrome C were found to be accelerated by PPIase [Lin, L-N., Hasumi, H. & Brands, J. F., Biochim. Botphys .Acta 956, 256-266 (1988)]. These results suggest that one species of PPIase can act upon limited species of protein substrates.

Although, based on the facts described above, the presence of multiple forms of PPIase acting on restricted kinds of proteins is presumed, the presence thereof has not been actually proved.

The theory that multiple forms of PPIase are present in one species of organism, and that the substrate specificity of a given PPIase, for example, from a mammal, which is constituted from a large number of cells endowed with highly differentiated functions, may differ from that, for example, of yeast which is a unicellular organism and *Escherichia coli* which is a prokaryote, is believed to be a logical conclusion in view of the different functions to be fulfilled by the different cells mentioned above.

The hypothesis that the action of CsA is modified through the inhibition of the PPIase activity has been proposed on the basis of the inhibitory effect of CsA on the porcine PPIase. To justify the hypothesis, it is important to clarify the question whether or not the activities of PPIases from many organisms of widely diverging phylogenic origins, for example, *Escherichia coli* and yeast, are inhibited by CsA. Moreover, it is not correlated yet between the distribution of the CsA-binding activity in lower organism and the inhibitory effect of CsA on their PPIases.

The presence of multiple forms of PPIases in various cells suggest that each PPIase acts on its specific substrates in each cell. This point, coupled with the finding that a cell specific form of PPIase may be present in the photoreceptor cells of Drosophila evidently acquires a profound significance in the use of a recombinant DNA for the production of a specific protein with a specific cell as a host. It is desirable that PPIases which affect the folding of the targeted protein or the process of the protein synthesis thereof, coexist with the targeted protein produced in the host cell. Generally, is is considered that the PPIase of the host cell effectively acts on the protein inherent in the host cell. Therefore, the PPIases and their genes of the *Escherichia coli* and yeast, which are frequently used as hosts for the production of useful substances by the recombinant DNA technology, may be useful for the purpose mentioned above. Various organisms are being studied for the presence of cyclophylin, using as an index the protein's ability to bond cyclosporin A, and the cyclosporin A bonding activity has been detected in arthropoda (cockroaches), trematoda, mollusks, molds, porifera, yeasts, and plants (pumpkins) as well as in mammals [Koletsky, A. J., Harding, M. W. & Handschumacher, R. E., J. Biol. Chem., 137, 1054–1059, 1986]. Nevertheless, no correspondence has been established between these activities and the PPIase activity.

Though it has been demonstrated that the porcine PPIase accelerates the folding of a protein, the question of whether or not the PPIase is actually present and exhibits the activity in the species, such as yeast and microbacteria, etc., and the question of the extent to which it participates in the folding of protein, has not been definitely answered. As one of the means for solving the numerous problems mentioned above, it is believed important to isolate PPIases from *Escherichia coli* and yeast, to study the nature of the PPIases as protein, and obtain the genes thereof.

SUMMARY OF THE INVENTION

As described above, examples have been found in which PPIases are associated with the folding of proteins. In these cases, however, only one species of PPIase has been identified for one species of organism, and thus the utility of the PPIase for the folding of protein has been limited.

This invention, therefore, is directed to providing two species of enzymes homogeneously isolated from *Escherichia coli* and an enzyme from yeast, and is further directed to providing genes coding for the enzymes and a method for producing the enzyme in a high yield by using the gene.

Specifically, this invention provides a yeast PPIase characterized by possessing the following properties: (1) acting on and isomerizing the peptide bond $X_{aa}$—Pro (wherein $X_{aa}$ stands for any amino acid and Pro stands for L-proline), (2) exhibiting a single molecular weight of about 17,000 daltons in the sodium dodecyl sulfate-polyacrylamide gradient gel electrophoresis, (3) exhibiting a single isoelectric point of about 6.2 in the isoelectric focusing, and (4) being inhibited by CsA; a method of producing the enzyme characterized by recovering from yeast cells of *Saccharomyces cerevisiae*; and a gene coding for the enzyme.

The present invention further provides an *E. coli* PPIase-$\beta$ characterized by possessing the following properties: (1) acting on and isomerizing the peptide bond $X_{aa}$—Pro (wherein $X_{aa}$ stands for any amino acid and Pro for L-proline), (2) exhibiting a single molecular weight of about 20,000 daltons in the sodium dodecyl sulfatepolyacrylamide gradient gel electrophoresis, (3) exhibiting a single isoelectric point of about 5.0 in the isoelectric focusing, and (4) not being inhibited by CsA; a method of producing the enzyme chasacterized by recovering from *E. coli* cells; a gene coding for the enzyme; and a method of producing the enzyme by using the gene.

The present invention also provides an *E. coli* PPIase-a characterized by possessing the following properties: (1) acting on and isomerizing the peptide bond $X_{aa}$—Pro (wherein $X_{aa}$ stands for any amino acid and Pro for L-proline), (2) exhibiting a single molecular weight of about 22,000 daltons in the sodium dodecyl sulfaepolyacrylamide gradient gel electrophoresis, (3) exhibitinq a single isoelectric point of about 9.7 in the isoelectric focusing, and (4) not being inhibited by CsA; and a method of producing the enzyme characterized by recovering from *E. coli* cells.

BRIEF DESCRIPTION OF THE DRAWINGS

FIG. 6 shows a nucleotide sequence of porcine PPIase used as a probe in screening a DNA coding for PPIase of the present invention, and an amino sequence estimated from the nucleotide sequence;

FIG. 7-1 and FIG. 7-2 show a nucleotide sequence of a gene derived from the yeast chromosome and coding for the PPIase of the present invention, and an amino acid sequence deduced from the nucleotide sequence;

FIG. 15 (a) shows result of separation of peptide fragments obtained from the cyanogen bromide cleavage of the PPIase-α using a reverse-phase Aquapore RP-300 column, and FIG. 15 (B) shows result similarly obtained from the PPIasβ.

FIG. 17-1 and FIG. 17-2, respectively, show a nucleotide sequence of a gene derived from E. coli and coding for the PPIase-β of the present invention, and a deduced amino acid sequence therefrom;

FIG. 18 shows a process for construction of a plasmid pBLΔEPPIb;

FIG. 19-1(A) shows a process for construction of an expressing plasmid pATtrp EPPIb, and FIG. 19-2(B) shows a nucleotide sequence of a linking region between a trpE promoter and PPIase gene in plasmid pATtrp EPPIb;

FIG. 25 shows the comparison between a natural PPIase-β and recombinant type PPIase (β) on a reverse phase Aquapore RP-300 column;

FIG. 27a+b shows the comparison of amino acid sequences of PPIases or cyclophylin from various origins; and, FIG. 28 shows hydropathy patterns of amino acid sequences of PPIases of various origins.

DESCRIPTION OF THE PREFERRED EMBODIMENT

Figure 1:
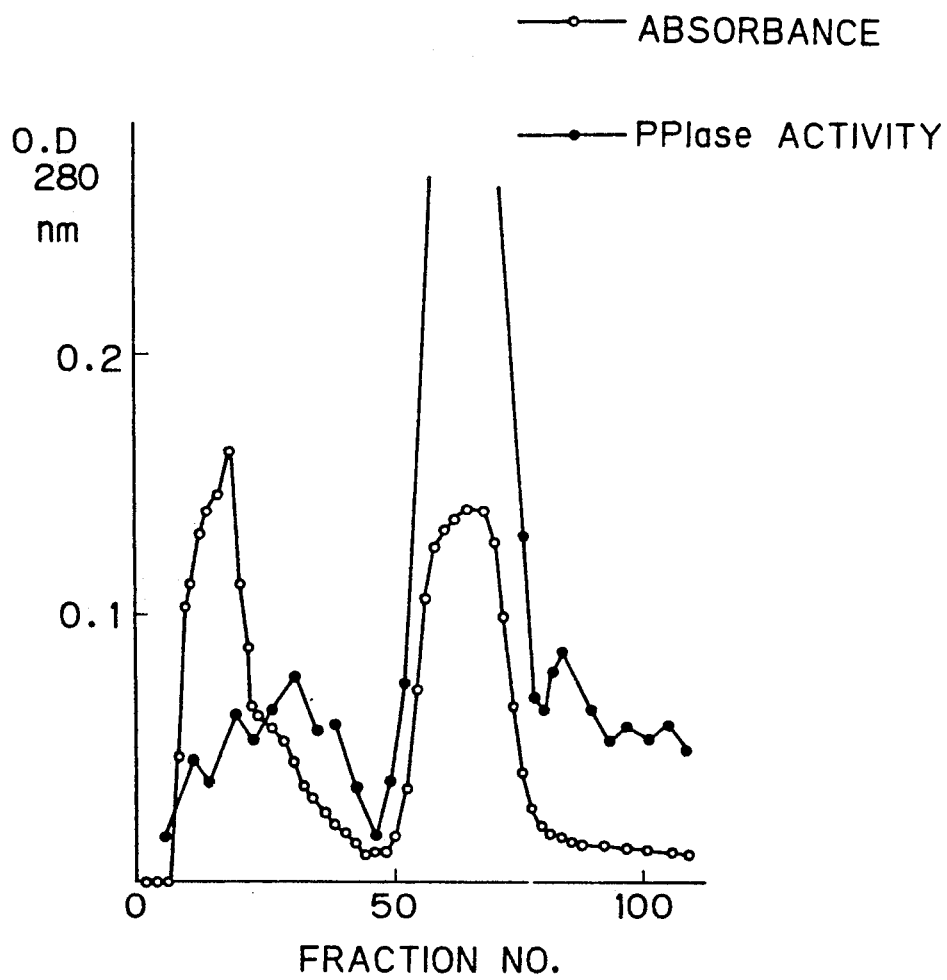
FIG. 1 is a graph showing the elution profile from a CM-Sepharose CL-6B column in the final purification step of yeast PPIase according to the present invention, wherein — o — indicates absorbance as 280 nm and — — indicates PPIase activity.

PPIase can be recovered from yeast cells by any conventional method of purifying an enzyme from microorganisms, and one such method will be described in detail in Example 1. Any yeast belonging to Saccharomyces, for example, Saccharomyces cerevisiae AH22 strain (ATCC 38626), can be used as a starting material.

A method of measuring PPIase activity has been described by N. Takahashi et al, Nature, 377, 473–475 (1989), and this method can be also used for the identification of the yeast PPIase of the present invention. More specifically, 2 ml of a 0.035M HEPES buffer containing 5 mM of 2 mercaptoethanol (pH 7.8) is placed in the spectrophotometer and is incubated for about 20 minutes until the temperature is stabilized at 25° C. Yeast PPIase and CsA (0.04 μg to 1 μg), are added in the cell and mixed for 1 minute . Then, 50 μl of 1.68 mM N-Succinyl-Ala-Ala-Pro-Phe-MCA are added and incubated for 30 seconds, and the reaction is started by adding 20 μl of 0.76 mM chymotrypsin. The effect of CsA on the inhibition of the PPIase activity can be detected by varying the amount of the CsA added. The kinetics of cis-trans isomerization of the substrate is monitored at 360 nm.

According to the present invention, yeast PPIase is purified by the method described in Example 1, and the purified yeast PPIase is characterized ln detail in Example 2.

A cDNA coding for porcine PPIase was prepared as a probe to isolate yeast PPIase gene coding by the method described in Example 3. This cDNA is analyzed for its nucleotide sequence. The amino acid sequence deduced from the cDNA nucleotide sequence has been confirmed to be completely identical to the amino acid sequence of porcine PPIase corresponding to valine at the 19 position through isoleucine at the 163 position, as reported in literature [Takahashi, N., Hayano, T. & Suzuki, M., Nature, 337, 473–475 (1989)].

A yeast chromosome DNA library was screened with the porcine PPIase cCNA described above as a probe and the DNA coding hybridized with the porcine cDNA was isolated. As a result of the determination of nucleotide sequence of this DNA, an open reading frame consisting of 161 amino acid residues from the translation initiation codon AT to the translation termination codon TAA has been identified. It has been confirmed that the aforementioned yeast chromosome DNA fragment codes for the yeast PPIase, based on the complete identity between the corresponding parts of amino acid sequence deduced from the DNA nucleotide sequence and the amino acid sequences of the tryptic fragments of the protein isolated from the aforementioned yeast.

By comparing the amino acid sequence of porcine PPIase determined as described in Example 3 and illustrated in FIG. 6, with the amino acid sequence of yeast PPIase determined as described in Example 4 and illustrated in FIG. 7, it has been confirmed that the PPIase of the present invention is a novel enzyme different from the known porcine PPIase.

The yeast PPIase of the present invention typically has an amino acid sequence illustrated in FIG. 7, but is not limited thereto. It includes enzymes wherein one or more amino acids in the amino acid sequence shown in FIG. 7 have been substituted with the other amino acids, and/or one or more amino acids have been added to the said amino acid sequence, and/or one or more amino acids have been removed from said amino acid sequence, and the same characteristics as those of the yeast PPIase are still retained.

The characteristics of the enzyme according to the present invention will be described in detail in Example 2.

The PPIase of this invention catalyzes the isomerization of prolyl peptide bond in protein and accelerates the folding of the protein and, therefore, can be used for converting a physiologically active polypeptide in the inactive form produced by the genetic manipulation into the active form with a correct conformation. Further, the physiologically active polypeptide of interest can be directly produced in the active form by inserting a gene coding for PPIase of the present invention in an expressible form, to a host to which has been inserted a gene coding for a physiologically active polypeptide in an expressible form, and then expressing the two genes in the same host. Moreover, it is useful as a reagent for studying the mechanism of action of CsA by the interaction of PPIase of the present invention with CsA, and as other research reagents.

The gene coding for PPIase of the present invention, is useful for the production of PPIase of the present invention by a genetic manipulation method, as well as in a modified form, as a gene material for the production of PPIase derivatives in which the enzymatic activity, stability, intracellular localizability, and substrate specificity thereof have been altered. Further, the gene according to the present invention is useful as a probe for screening a gene coding for other PPIase enzymes.

The recovery of the PPIase from *E. coli* can be accomplished by any of methods conventionally used for obtaining an enzyme from microorganisms. One of such methods is described specifically in Example 1. Any of the known strains, e.g., *E. coli* ST 249 strain [Kajie, S., Miki, K., Lin, E.C.C. & Anraku, Y., PEMS Microbiol. Lett., 24, 25–29 (1984)] may be used as the starting material.

According to the present invention, two PPIase components, i.e., PPIase-β as a main component and PPIase-α as a minor component, are used.

These PPIases are treated with trypsin and cyanogen bromide, the amino acid sequences of the fragments determined, and the N-terminal amino acid sequences determined by a conventional method, to characterize PPIases in amino acid sequences. An oligonucleotide probe is designed on the basis of the information from the amino acid sequences of the PPIase-β protein.

Then, a gene coding for PPIase of the present invention is obtained by screening a DNA library from *E. coli* with the said oligonucleotide probe. A nucleotide sequence of the cloned DNA is determined. The agreement between the corresponding part of the amino acid sequence estimated from the above nucleotide sequence and the amino acid sequence of the tryptic fragment of the protein (β) isolated from *E. coli* demonstrates that the DNA derived from *E. coli* encode the *E. coli* PPIase-β.

Further, the comparison of the determined amino acid sequence with the amino acid sequences of the known PPIases demonstrates that the PPIase-β is a novel enzyme different from the known PPIases.

Similarly, PPIase-α of the present invention has been confirmed to be a novel PPIase on the basis of the comparison with the amino acid sequences of the known PPIases.

The PPIase-β of the present invention possesses the amino acid sequence shown in FIG. 17.

The characteristics of the enzyme of the present invention will be described in detail in Examples 6 and 7.

The PPIase of the present invention catalyzes the isomerization of the prolyl peptide bond in protein and accelerates the folding of the protein and, therefore, can be used for converting a physiologically active polypeptide in inactive form produced by genetic manipulation into a correct conformation of active form. Further, the physiologically active polypeptide of interest can be produced directly in the active form by inserting a gene coding for the PPIase of this invention in an expressible form to a host to which had been inserted a gene coding for a physiologically active polypeptide in an expressible form, and expressing the two genes in the same host. Wherein two different kinds of enzyme are provided within one species, the different enzymes suitable for the activation by accelerating the folding of different proteins within the same species, can be made available independently. Since the PPIase of the present invention does not interact with CsA, it is useful as a reagent for studying the mechanism of action of CsA in comparison with PPIase from mammal or yeast on inhibition by CsA, and as other research reagents.

The gene coding for PPIase of the present invention, is useful for the production of the PPIase of the present invention by the genetic manipulation, as well as in a modified form, useful as a gene material for the production of PPIase derivatives in which the enzymatic activity, stability, intracellular localizability, and substrate specificity thereof are altered. Moreover, the gene of the present invention is useful as a probe for screening a gene coding for other PPIase enzymes.

When the aforementioned gene is used to produce a PPIase in a microorganism host, such as recombinant *Escherichia coli*, as described in Examples 9 to 11, the PPIase can be produced much more efficiently than that extracted from non-recombinant *E. coli*. The PPIase thus produced using the recombinant possesses the same characteristics as the PPIase extracted from non-recombinant *E. coli*, as described in Example 13.

EXAMPLES

For a more specific illustration of the present invention, the following examples are presented. These are intended to be merely illustrative of and do not in any sense limit the invention.

EXAMPLE 1

Purification of Yeast PPIase

In 700 ml of a 10 mM EDTA solution containing 1 mM phenylmethyl sulfonyl fluoride, 700 g of cells of *Saccharomyces cerevisiae* AH22 were suspended, and disrupted with a French press at the maximum pressure of 2,200 psi. The resultant suspension was centrifuged at 18,000 rpm for 40 minutes. The supernatant was saturated with 80% ammonium sulfate to precipitate proteins. The precipitate was collected by centrifugation and then dissolved in 380 ml of 10 Tris HCl buffer, pH 8.0, containing 0.05% NaN$_3$. The concentrated sample was dialyzed against 10 mM Tris-HCl buffer (pH 8.0) containing 0.05% NaN$_3$. The internal dialyzate was applied on a DEAE-Toyopearl column (5 cm in diameter×20 cm) equilibrated with the same buffer. Elution was carried out with the same buffers containing 0.05M, 0.1M, 0.2M, 0.3M, and 0.5M of sodium chloride, as a stepwise increase of the sodium chloride concentrations in the order. The eluents were passed at a flow rate of 32 ml/hour, and fractions of 16 ml each were collected. These fractions were tested for PPIase activity by the aforementioned method (N. Takahashi et al., Nature, 377, 473–475, 1989). As a result, it was found that the PPIase activity was present in the eluent passed through the column and the eluent with 0.1M sodium chlorlde containing a buffer. The relative distribution of PPIase was 5 in the eluent with the 0.1M sodium chloride eluent based on that of the passed through eluent as 100.

Then, the passed through fraction was applied on a Sephadex G-75 column (2.5 cm in diameter×90 cm) previously equilibrated with 10 mM Tris-HCl buffer (pH 8.0) containing 0.05% NaN$_3$ and 0.15M NaCl, and was eluted with the same buffer. The elution was carried out at a flow rate of 10 ml/hour, and 5 ml of each fractions were collected. As a result of testing these fractions for the PPIase activity by the aforementioned method, it was confirmed that PPIase activity was present in a fraction corresponding to a molecular weight of about 20,000.

Then, the active fraction was dialized against 10 mM sodium acetate buffer (pH 6.0). The internal dialyzate was applied on a CM-Sepharose CL-6B column (2.5 cm in diameter×40 cm) previously equilibrated with the same buffer, and eluted with the same buffer.

The elution was carried out at a flow rate of 20 ml/hour, and 10 ml of each fraction was collected.

An elution profile is shown in FIG. 1. A finally purified yeast PPIase was obtained by combining the active fractions, NOS. 52 to 76, shown in FIG. 1.

EXAMPLE 2

Characterization of Yeast PPIase (1) Determination of molecular weight

Figure 2:
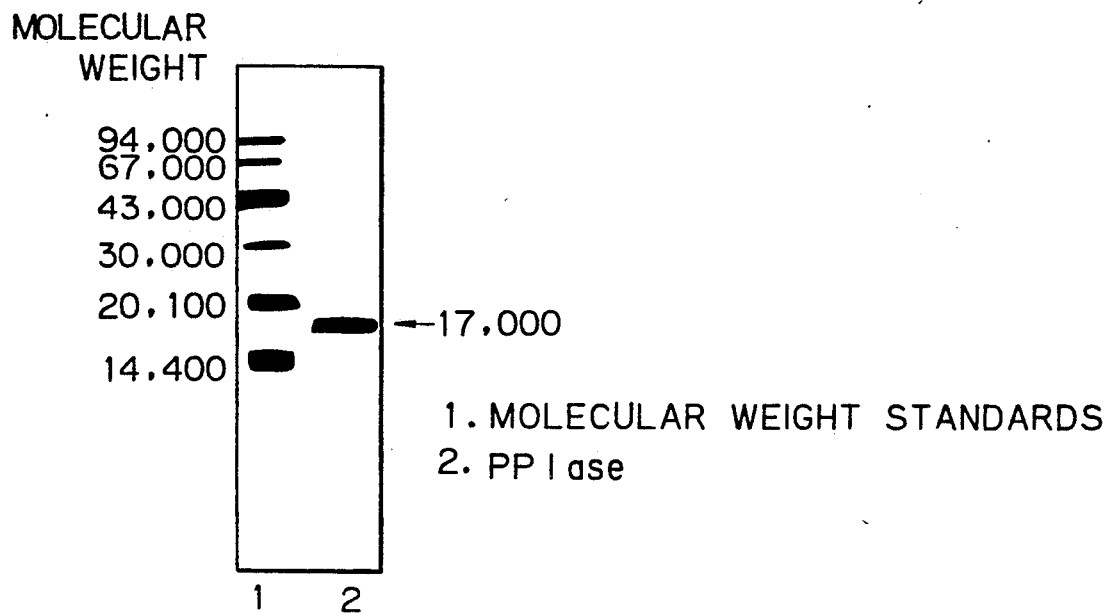
FIG. 2 shows an electrophoretic pattern obtained by subjecting the yeast PPIase of the present invention to SDS-polyacrylamide concentration gradient gel electophoresis.

Molecular weight of the PPIase obtained in Example 1 was determined by a sodium dodecyl sulfate-polyacrylamide concentration gradient gel (12 to 30% polyacrylamide gel) electrophoresis. As molecular weight standards, phosphorylase b (molecular weights 94,000), bovine serum albumin (67,000), ovalbumin (43,000), carbonic anhydrase (30,000), soybean trypsin inhibitor (20,100), and α-lactalbumin (14,400) were used. The PPIase was found to possess a single molecular weight of about 17,000 daltons, as shown in FIG. 2.

(2) Determination of the Isoelectric Point

Figure 3:
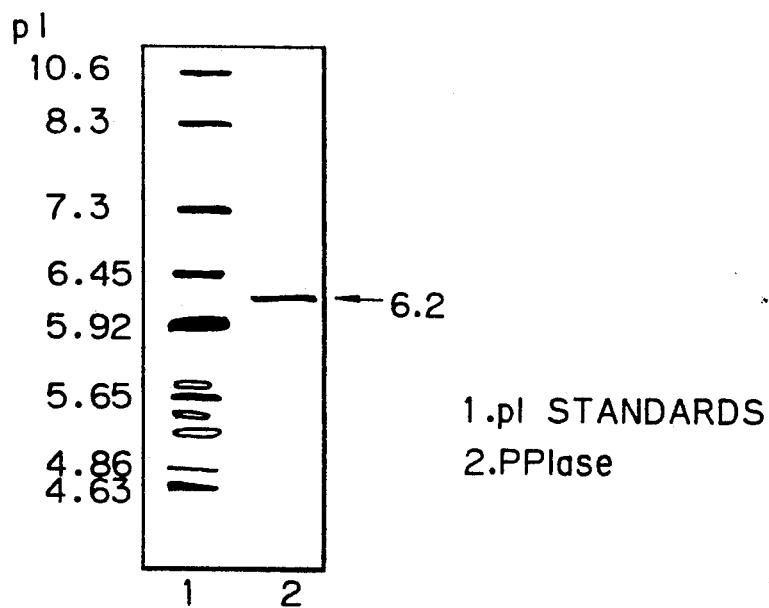
FIG. 3 shows an electrophoretic pattern obtained by subjecting the yeast PPIase of the present invention to isoelectric focusing.

The isoelectric point of the PPIase obtained in Example 1 was determined by isoelectric point electrophoresis in a manner described in the Ampholline Isoelectric Point Electrophoresis Manual (LKB Co.,), using cytochrome C (pI: 10.6), whale myoglobin (8.3), equine myoglobin (7.3), porcine myoblogin (6.45), porcine trifluoroacetyl myoglobin (5.92), azurine (5.65), C-phycocyanin (4.85), and C-phycocyanin (4.65) as standards. As a result, the PPIase of the present invention was found to have a single isoelectric point of about 6.2, as shown in FIG. 3.

(3) Homogeneity in Reversed-phase Column, Chromatography

Figure 4:
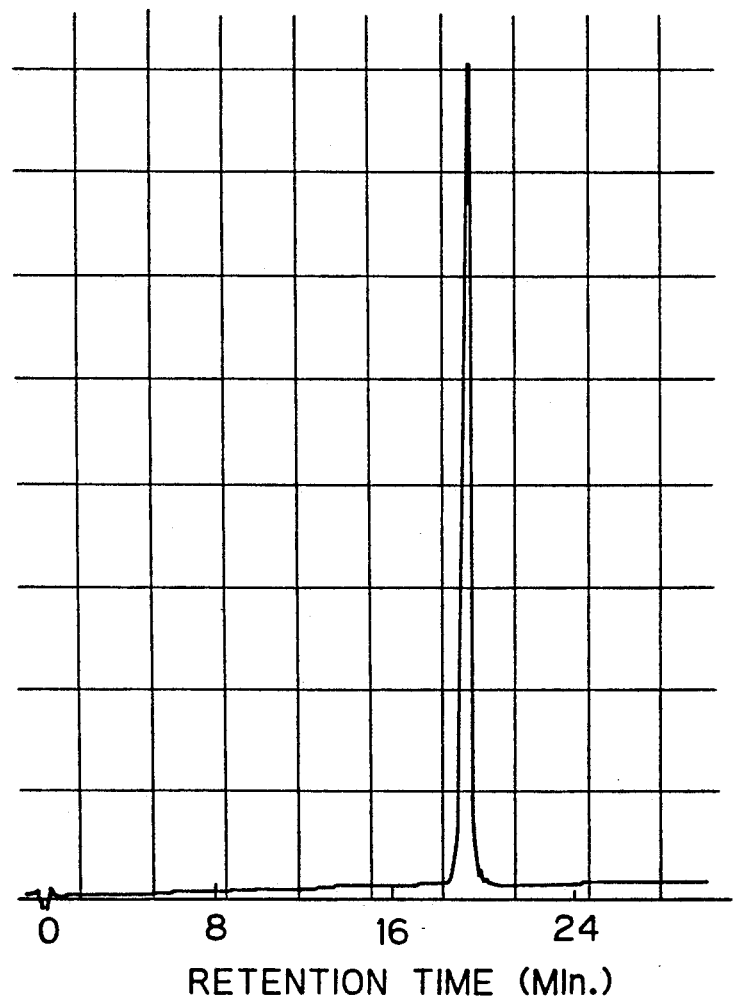
FIG. 4 shows the results of a purity test on the yeast PPIase of the present invention using a reverse-phase Aquapore RP-300 column.

PPIase of the present invention was applied on a reverse-phase Aquapore RP-300 column (2.1 mm in diameter×3 cm; produced by Applied Biosystems Corp.), and eluted with 0.1% trifluoroacetic acid containing acetonitrile in an increasing concentration of linear gradient of 0% to 100% over a period of 45 minutes, at a flow rate of 200 ml/min. As shown in FIG. 4, the PPIase of this invention gave a single peak.

(4) Determination of Partial Amino Acid Sequence

Intact PPIase

A sample of PPIase obtained in Example 1 was analyzed with an automatic amino acid sequencer, Model 477A (produced by Applied Biosystems). The analysis detected no amino acid, indicating that the N-terminal of the purified enzyme was protected.

Amino Acid Sequences of Tryptic Fragments

To a solution of 200 μg of yeast PPIase dissolved in 50 μl of 0.1M NH$_4$HCO$_3$, 4 μg of TPCK treated trypsin was added, and a hydrolysis reaction was carried out at 37° C. for 8 hours. The resultant hydrolyzate was separated and purified by using a reverse-phase Spheri 5RP-18 column (2.1 mm in diameter×3 cm; produced by Applied Biosystems). The elution was carried out with a 0.1% trifluoroacetic acid containing acetonitrile with a concentration gradient of 0% to 100%, at a flow rate of 200 μl/min, to obtain nine peptide fragments.

The amino acid sequences of these peptide fragments were determined using the aforementioned automatic sequencer Model 477A, and the following amino acid sequences were obtained:

(1) Val-Val-Phe-Lys
(2) Thr-Ala X-Asn-Phe-Arg
(3) Ala-Leu-X-Thr-Gly-Glu-Lys
(4) Gly-Phe-Gly-Tyr-Ala-Gly-Ser-Pro
(5) Val-Ile-Pro-Asp-Phe-Met-Leu-Gln-X-Gly-Asp-Phe-Thr-Ala-Gly-Asn-Gly-Thr-X-Gly-Lys
(6) His-Val-Val-Phe-Gly-Glu-Val-Val-Asp-Gly-Tyr-Asp-Ile-Val-Lys
(7) Lys-Val-Glu-Ser-Leu-Gly-Ser-Pro-Ser-Gly-Ala-Thr-Lys
(8) Ile-Val-Val-Ala-Lys
(9) Ser-Gly-Glu-Leu (5) Amino Acid Composition To 20 μg of purified PPIase was added 0.5 ml of 6N HCl, and the mixture was degassed, sealed in a tube, and hydrolyzed at 110° C. for 24 hours. The resultant hydrolyzate was evaporated under a vacuum, and analyzed for amino acid composition by using an amino acid analyzer. The results are shown in Table 1.

TABLE 1

| Amino acid composition of yeast PPIase | | |
|---|---|---|
| Amino acid | Molar ratio | Molar ratio (from amino Acid sequence) |
| Asp | 16.24 | (17) |
| Thr | 7.52 | (8) |
| Ser | 7.97 | (9) |
| Glu | 12.86 | (11) |
| Gly | 22.42 | (23) |
| Ala | 10.00 | (10) |

TABLE 1-continued

Amino acid composition of yeast PPIase

| Amino acid | Molar ratio | Molar ratio (from amino Acid sequence) | |
|---|---|---|---|
| Cys | — | (2) | |
| Val | 10.19 | (15) | Val—Val bonds at four positions |
| Met | 1.95 | (2) | |
| Ile | 5.68 | (7) | |
| Leu | 7.21 | (8) | |
| Tyr | 4.27 | (5) | |
| Phe | 11.57 | (12) | |
| His | 3.82 | (4) | |
| Lys | 12.19 | (12) | |
| Arg | 4.89 | (5) | |
| Pro | 8.91 | (10) | |
| Trp | — | (1) | |

(6) Sensitivity of Yeast PPIase to Cyclosporin A (CsA)

Figure 5:
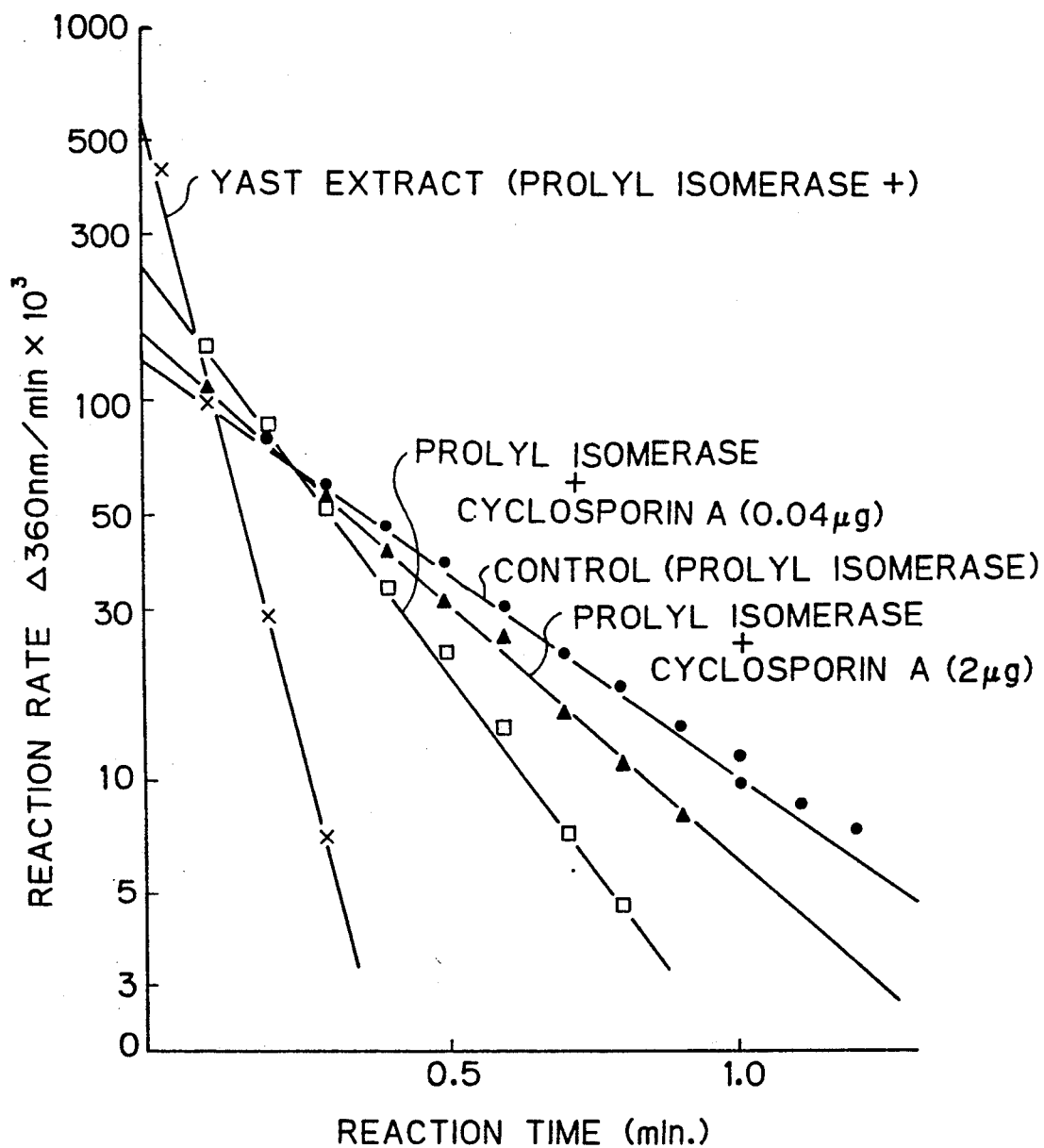
FIG. 5 is a graph showing an inhibition of the yeast PPIase of the present invention by CsA.

Inhibition effect of CsA on an activity of the purified yeast PPIase was examined by the method disclosed in N. Takahashi et al., Nature, 377, 473–475 (1989). The results are shown in FIG. 5. It is clear that the yeast PPIase is inhibited by an immunosuppressive agent CsA and the inhibition constant is about $10^{-8}$M. In this figure, the longitudinal axis is an amount of change in absorbance at 360 nm per unit time, namely the reaction rate, on a logarithmic scale, and the horizontal axis is the reaction time. Therefore, the data indicate that the enzyme potency increases with an increase of a slope of the change in the reaction rate, and that a degree of inhibition by CsA increases as the slope decreases and approaches a slope in the absence of enzyme.

The fact that the inhibition by CsA of PPIase purified from yeast has been demonstrated means that the interrelation between the binding activity of CsA and the inhibition effect of PPIase has been established with respect to not only mammals but also yeasts. It is thus suggested that, not only the immunosuppressive action of CsA but also, e.g., the mycotic action possessed by CsA, is exhibited through the inhibition of the enzymatic activity of PPIase.

EXAMPLE 3

Cloning of Porcine PPIase Gene

For obtaining a clone containing a porcine PPIase cDNA, a porcine liver cDNA library prepared using λ gtll obtained from Clontech Corp., U.S.A. as a vector was used. $4 \times 10^4$ pfu of λ recombinant phages were added to 50 μl of an overnight culture of Escherichia coli Y 1090 [LB culture medium (1% trypton, 0.5% yeast extract, and 0.5% NaCl)+0.2 maltose], allowed to react at 37° C. for 20 minutes, and then spread in combination with 3 ml of L-Top-Agarose (LB culture medium+0.7% agarose) onto four L-plates (LB culture medium+1.5% agar) 90 mm in diameter. The plates were incubated at 37° C. overnight to form plaques, and then preserved at 4° C. for 1 hour. The recombinant phage was transferred onto a membrane filter (produced by Amersham Corp.; "Hybond-N"), and the membrane filter was placed on a filter paper (produced by Whatman Corp; "3MM") impregnated with 0.5N NaOH and 1M NaCl for 5 minutes, and then placed on a filter paper impregnated with 1M Tris-HCl (pH 7.5) 1.5M NaCl for 5 minutes. The resultant phage DNA was fixed on the filter by washing the filter with a 2×SSC (20×SSC represents 3M NaCl and 0.3M trisodium citrate) solution, air drying, wrapping with Saran Wrap, and exposing to the UV light. The phage DNA on the filter was screened by a plaque hybridization using a synthetic oligonucleotide [specific activity $\geq 10^7$ cpm/μg] labeled with a $^{32}$P radioisotope as a probe [Benton & David, Science, 196, 180–182 (1977)].

As a probe, a probe DNA 5'-TCC ATT GC(TC) TCC AC(AGT) AT(AG) TTC AT-3', corresponding to an amino acid sequence from methionine at the 135 position to methionine at the 141 position of porcine PPIase [Takahashi et al, Nature, 337, 473–475 (1989)], was synthesized using an automatic DNA synthesizer (Applied Biosystems Model 380B) based on the phosphoamidite method developed by Caruthers et al. [Matteucci, M. D. and Caruthers, M. H., Tetrahedron letters 21, 719 (1980)]. By treating the synthetic DNA (21 pmoles) in 50 μl of a solution containing 50 mM Tris-HCl (pH 7.6), 10 mM MgCl$_2$, 5 mM dithiothreitol, 100 μCi [λ-$^{32}$P]ATP (3000 Ci/mmol, Amersham Corp), and 12 units of T$_4$ polynucleotide kinase (Takara Shuzo Co., Ltd.) at 37° C. for 60 minutes, the 5'-terminal thereof was labeled through phosphorylation. A hybridization was carried out using a solution containing 6×SSC, 5×Denhardt solution (100×Denhardt solution: 2% bovine serum albumin, 2% Ficoll and 2% polyvinyl pyrrolidone), 0.5% SDS, and 50 μg/ml of sonicated salmon sperm DNAs, and $10^6$ cpm/ml of probe DNA at 37° C. for 16 hours. The filter was washed with 2×SSC at 37° C., and exposed by contact with an X-ray film (Kodak, "XAR-5") at −70° C. for 10 hours.

After the development, four plaques giving a positive signal were scraped off with the tip of a Pasteur's pipet, suspended in 100 μg of a TM solution [10 mM Tris-HCl (pH 7.5), 10 mM MgCl$_2$], and left standing at a room temperature for 20 minutes. 0.5 μl of the suspension was diluted with 1 ml of the TM solution, and Escherichia coli Y 1090 strain was infected with 5 μl of the mixture by the method described above, and spread on an L-plate to form plaques. The formed plaques were subjected to the hybridization as described above, to obtain a positive clone as a single plaque. The positive plaque was scraped off with the tip of a Pasteur's pipet, mixed with 50 μl of Y 1090 cells, left standing at 37° C. for 20 minutes, and shaken and cultured in 2 ml of an LB culture medium containing 10 mM MgSO$_4$ at 37° C. for 6 hours. After an addition of 100 μl of chloroform, the mixture was treated with a vortex mixer for complete bacteriolysis, and then centrifuged at 5,000 rpm for 5 minutes. The obtained supernatant contained the phage on the order of $10^{10}$. To 800 μl of the supernatant were added 100 μl of 5M NaCl and then 540 μl of isopropanol, the mixture was thoroughly mixed, left standing at −20° C. for 20 minutes, and then centrifuged at 15K rpm for 5 minutes. The precipitate thus obtained was washed with 500 μl of 70% ethanol and dissolved in 200 μl of a TE solution [10 mM Tris-HCl (pH 8.0), 1 mM EDTA]. To the solution were added 1 μl (60 units/μl) of DNase I from Takara Shuzo Co., Ltd.) and 2 μl of 1M MgCl$_2$, and the mixture allowed to react at 37° C. for 30 minutes. After adding 100 μl of a TE-saturated phenol, the mixture was treated with a vortex mixer, and centrifuged at 12K rpm for 5 minutes. The aqueous phase was separated and extracted once with phenol/chloroform (1:1), and after adding 20 μl of 3M sodium acetate (pH 5.2) and 500 μl of ethanol, centrifuged to precipitate DNA. This precipitate was washed with 70% ethanol, dried under a vacuum, and dissolved in 50 μl of TE. By the procedure described above, a phage DNA was obtained in an amount equivalent to 1

μg. To 20 μl of the resultant DNA solution were added 2.5 μl of a 10×EcoRI buffer [0.5M NaCl, 1M Tris-HCl (pH 7.5), 70 mM MgCl$_2$], and 1 μl (20 units) of EcoRI (from Nippon Gene) and 1 μl of 10 mg/ml of RNase A (from Sigma Co.). The mixture was allowed to react at 37° C. for 1 hour, and subjected to 0.7% agarose electrophoresis, and DNA bands formed were blotted on a Hybond filter according to the Southern blot method [Southern, E. *J. Mol Biol.*, 98, 503-517 (1975)]. The DNAs bonded on the filter were subjected to hybridization under the same conditions as those of the plaque hybridization. Each clone thus obtained possessed about 700 bp of EcoRI fragment. The DNA was separated from the agarose and purified by the glass powder method (Bio-101 Corp., Gene Clean TM) and then subcloned into a pUC19 vector.

In a total volume of 30 μl of a reaction solution [66 mM Tris-HCl (pH 7.6), 6.6 mM MgCl$_2$, 10 mM dithiothreitol, 1 mM ATP] containing 2.8 units of T$_4$ DNA ligase (from Takara Shuzo Co., Ltd.), a pUC19 vector (30 ng) digested with EcoRI and a recovered 700 bp EcoRI fragment (20 ng) were treated at 16° C. for 4 hours, to obtain a recombinant plasmid. A portion, 10 μl, of the reaction solution was used to transform *Escherichia coli* JM107 strain as a host bacteria. The sensitive *Escherichia coli* strain used for this transformation was produced by a calcium chloride method [Mandel, M. and Higa, A., *J. Mol. Biol.*, 53, 159-162 (1970)]. More specifically, an overnight culture (LB culture medium) of *Escherichia coli* JM107 strain was 100-fold diluted with the same culture medium, and shaken and cultured at 37° C. until OD$_{600}$ reached 0.6. Then, 1.5 ml of the resultant culture was centrifuged at 5000 rpm for 5 minutes to collect the cells. the cells were suspended in 750 μl of a 50 mM CaCl$_2$, left standing on ice for 20 minutes, and centrifuged. The precipitate was resuspended in 100 μl of a 50 mM CaCl$_2$, and after adding the aforementioned DNA ligase reaction solution, the mixture was left standing on ice for 40 minutes and incubated as 42° C. for 1 minute. After adding 1 ml of an LB culture medium, the mixture was left to stand at 37° C. for 30 minutes. Next, 0.1 ml of the culture was spread on an X-Gal plate (an L plate containing 155 μg/ml of 5-bromo-4-chloro-3-indolyl-β-D-galactopyranoside, 80 μq/ml of isopropyl-β-D-thiogalactopyranoside and 25 μg/ml of ampicillin and incubated at 37° C. overnight. Among colonies produced on the plate, those having a white color were selected. One platinum spatula full of the cells was transferred onto an LB culture medium containing ampicillin (25 μg/ml), and cultured overnight 1.5 ml of the overnight culture was centrifuged for collection of cells. Minipreparation of a plasmid DNA was carried out by the standard method [Maniatis et al., Molecular Cloning: A Laboratory Manual, 1982]. The obtained plasmid DNA was cleaved with an EcoRI and subjected to agarose gel electrophoresis, to confirm that the 700 bp EcoRI fragment had been inserted in pUC vector. Further, by the Southern blot method, is was confirmed that this fragment would hybridize with the probe.

Using a PstI restriction enzyme recognition site present in the inserted DNA, 1 μg of a plasmid DNA was subjected to double digestion in 25 μl of a solution [containing 50 mM NaCl, 100 mM Tris-HCl (pH 7.5), 7 mM MgCl, 20 units of EcoRI (Nippon Gene), and 20 units of EcoRI (Nippon Gene), at 37° C. for 60 minutes, and about 560 bp DNA fragment was incorporated in pUC18 vector at the EcoRI and PstI site, to obtain a pUC-pPPI. By incorporating the DNA fragment containing the insert to the M13mp type phage DNA and deciding the nucleotide sequence by the dideoxy method [Sanger, F., Nicklen, S., and Corison, A. R., *Proc. Natl. Acad. Sci. USA*, 74, 5463-5467 (1977)], the desired cDNA coding for the porcine PPIase was identified. The amino acid sequence estimated from this cDNA agreed completely with the portion of the reported porcine PPIase from valine at the 19 position to isoleucine at the 163 portion. The nucleotide sequence and the amino acid sequence estimated therefrom is shown in FIG. 6.

EXAMPLE 4

Cloning of Yeast PPIase Gene

For obtaining a clone containing a yeast PPIase gene, a yeast chromosome DNA library prepared using λ gtll (Clontech Corp., U.S.A.) as a vector, was used. *E. coli* Y 1090 strain as a host was infected with λ gtll recombinant phase, and a total 4×10$^4$ of transformed plaques were formed on an L-plate. The recombinant DNA was transferred onto a membrane filter (from Amersham Corp., "Hybond- N") and screened with plaque hybridization [Benton & Davis, *Science*, 196, 180-182 (1977)] using a porcine PPIase cDNA (specific activity≧10$^8$ cpm/μg) labeled with a $^{32}$P radioisotope as a probe.

The probe was prepared by labeling tha EcoRI-PstI fragment of the porcine PPIase cDNA shown in FIG. 6 with a random primed DNA labeling kit (from Boehringer Corp.) according to the manufacturer's manual. The hybridization was performed in a solution containing 6×SSC, 5×Denhardt solution, 0.5% SDS, 50 μg/ml of a sonicated salmon sperm DNA, and 10$^6$ cpm/ml of the probe DNA at 50° C. for 16 hours. The membrane filter was washed 2×SSC at 50° C., and exposed by contact with an X-ray film (Kodak, "XAR~5") at −70° C. for 10 hours. By repeating the hybridization procedure on positive plaques, a positive clone was obtained as a single plaque.

From this clone, a phage DNA was prepared using the method proposed by Blattner et al. [*Science*, 202, 1279-1284 (1978)]. One μg of the phage DNA was digested by treating with 25 μl of a solution [50 mM NaCl, 100 mM Tris-HCl (pH 7.5), 7 mM MgCl$_2$, 20 units of EcoRI (from Nippon Gene)] at 37° C. for 60 minutes, and a Southern blot of the digest was hybridized with a probe [Southern, E., *J. Mol. Biol.*, 98, 503-517 (1975)]. A hybridized fragment had a size of about 2.4 kb, recovered from agarose by the glass powder method (Bio-101 Corp., Gene Clean TM), and then subcloned into the pUC19 vector.

By ligating the EcoRI-digested pUC19 vector (30 ng) and the recovered 2.4-kb EcoRI fragment (20 ng) using 2.8 units of T$_4$ ligase (Takara Shuzo Co.) in a total 30 μl of a reaction solution [66 mM Tris-HCl (pH 7.6), 6.6 mM MgCl$_2$, 10 mM dithiothreitol, 1 mM ATP] at 16° C. for 4 hours, to obtain a recombinant plasmid. *E. coli* JM107 strain was transformed with 10 μl of the reaction mixture, and spread on an X-Gal plate to form colonies. White colored colonies were selected, inoculated to 5 ml of an LB culture medium containing 25 μg/ml of ampicillin, and cultured at 37° C. overnight. From 1.5 ml of the overnight culture DNA was prepared by the mini-preparation method. The DNA was cleaved with EcoRI and subjected to agarose gel electrophoresis, to identify a recombinant plasmid containing a proper inserted DNA. This inserted DNA was digested with the restriction enzymes, Xba I and Pst I. On analysis by the Southern blot method, it was confirmed that an about 1.4 kb Xba I fragment containing a Pst I recognition site was hybridized with the probe.

The products from double digestion of the inserted DNA with the Pst I and Xba I, i.e., the DNA fragments about 750 bp and 650 bp in size, were incorporated in the M13mp type phage DNA, and assayed by the dideoxy method to determine the nucleotide sequences, respectively. There was obtained a gene highly homologous to the porcine PPIase cDNA.

The amino acid sequence estimated from the nucleotide sequence of the above gene implies that the gene encodes a protein consisting of 162 amino acid residues. This amino acid sequence has been found to agree with the amino acid sequence of any of the peptides obtained from enzymatic cleavage of proteins, indicating that the gene obtained above is a gene coding for the main component of the yeast PPIase.

The molecular weight of this protein calculated from the deduced amino acid sequence (consisting of 162 amino acids from N- terminal methionine residue to C-terminal leucine residue) is 17,453 daltons. The amino acid composition satisfactorily agreed With the found value.

*Escherichia coli* JM107/pUC-y-PPI containing plasmid pUC-y-PPI has been deposited at the Fermentation Research Institute, Agency of Industrial Science and Technology under FERM P-10812.

EXAMPLE 5

Purification of *E. coli* PPIase

Figure 8:
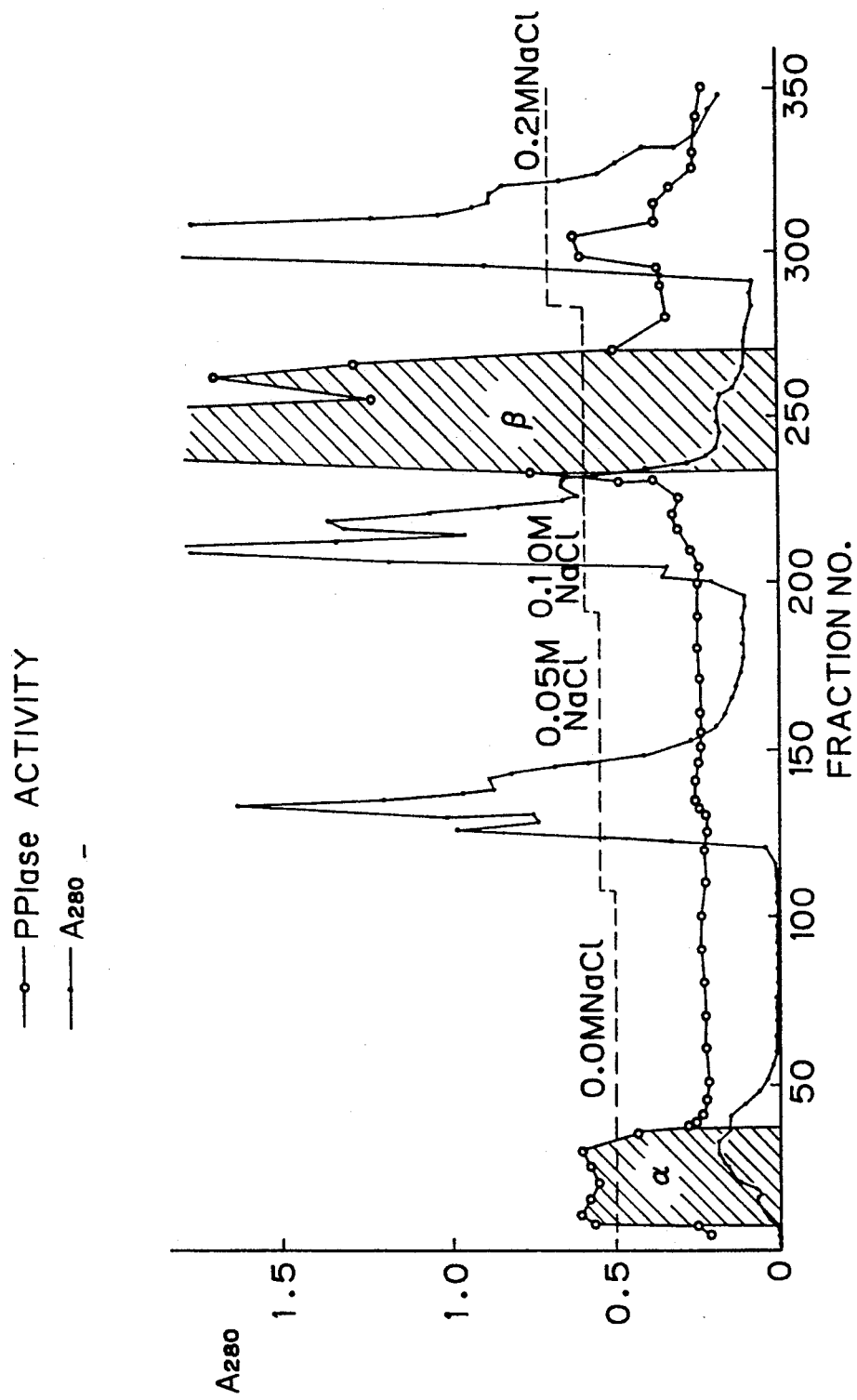
FIG. 8 shows an elution profile in separation of E. coli extract, using a DEAE-Sepharose CL-6B column.

In 500 ml of a 0.1M Tris-HCl buffer (pH 7.8) containing 5 mM 2-mercaptoethanol, 200 g of an *Escherichia coli* (ST 249 strain) cultured under anaerobic conditions was suspended, with repeated two cycles of freezing and thawing treatments, and then stirred with Polytron. The suspension was treated with 2 g of lysozyme at room temperature for 30 minutes, stirred with Polytron, and centrifuged. To the supernatant was added ammonium sulfate to 80% saturation, and was left standing as 4° C. overnight. The resulting precipitate was collected by centrifugal separation, suspended in 10 mM Tris-HCl buffer (pH 7.8) containing 0.05% NaN$_3$, dialyzed against the same buffer and then subjected to centrifugal separation. After removal of precipitate in the dialysate, tho supernatant was applied on an ion-exchange DEAE-Sepharose CL-6B column (2.5 cm in diameter × 40 cm). The peptidyl prolyl cis-trans isomerase (PPIase) activity was measured by the method described in Takahashi, N. et al., *Nature*, 337, 473–475 (1989). The elution of the sample from the column was effected by increasing sodium chloride concentrations by stepwise to 0.05M, 0.1M, 0.2M, 0.3M, and 0.5M. The elution was carried out as a flow rate of 20 ml/hr. The elution profile obtained from the DEAE column chromatograph is shown in FIG. 8. The *E. coli* PPIase activity was detected in the pass through fraction (salt concentration, 0M) and the fraction eluted with a salt concentration of 0.1M. Of the total amount of activity, about 10% was obtained in the pass through fraction and about 90% in the fraction eluted with a salt concentration of 0.1M. The component in the pass through fraction is referred to as a minor component (α) and that in the fraction eluted with a salt concentratton of 0.1M as a main component (β).

Figure 9A:
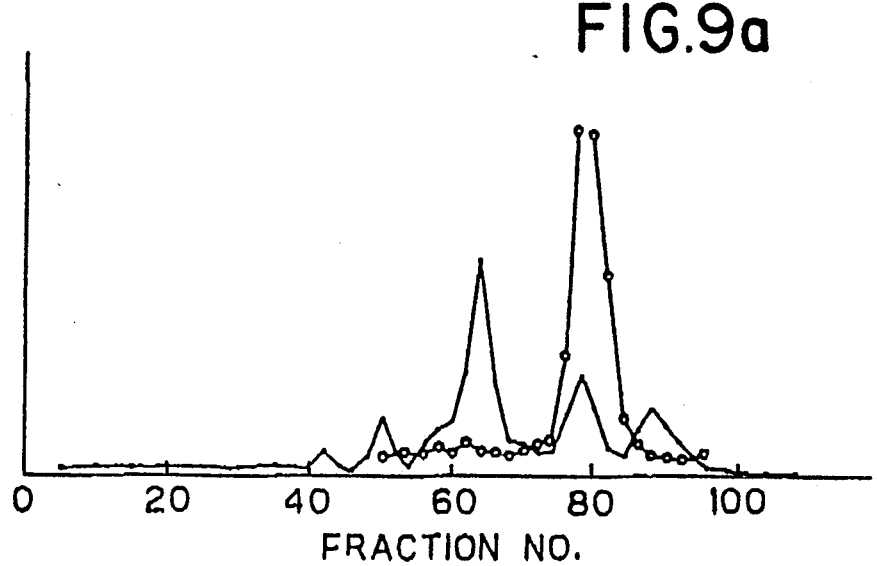
FIG. 9 (a) shows an elution profile in purification by gel filtration of a minor fractton (a-fraction) shown in FIG. 8 with Sephadex-G75 column, wherein — ● — indicates the elution of protein detected by absorbance at 280 nm and — o — indicates the elution of the PPIase activity, and FIG. 9 (b) is a diagram showing the results similarly obtained from the main fraction (β-fraction) shown in FIG. 8.
Figure 9B:
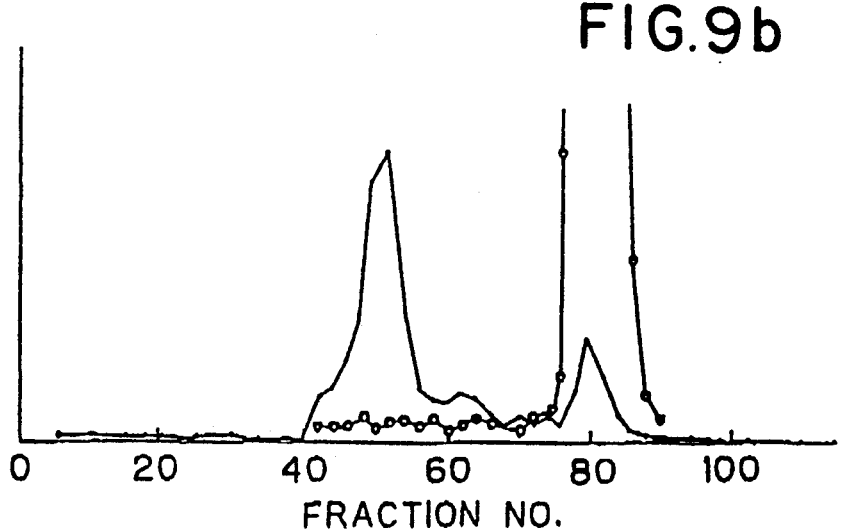
Figure 10:
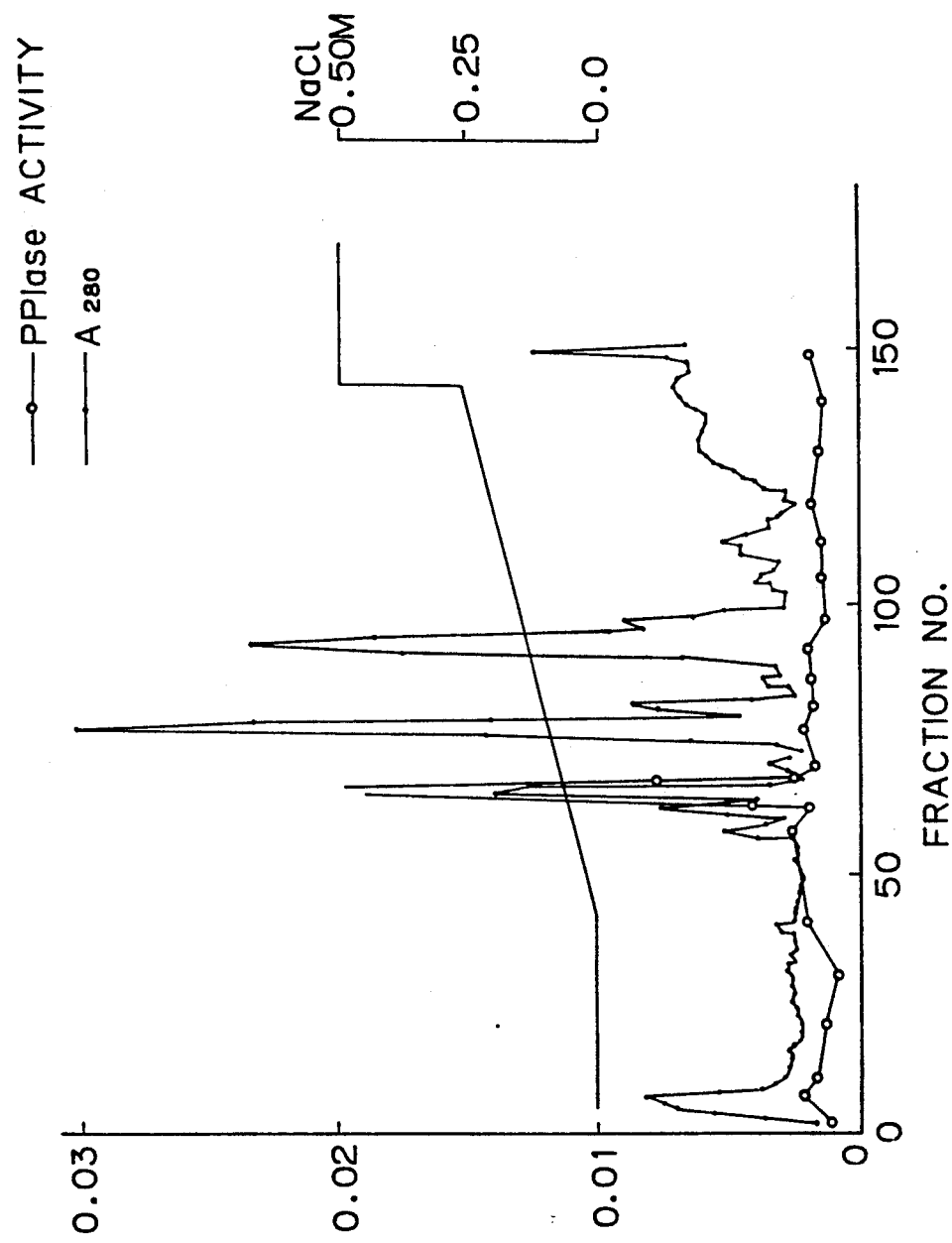
FIG. 10 shows an elution profile.-an further purification of the PPIase-α fraction separated according to FIG. 9 (a), using a CM-Sepharose CL-6 column.

The two fractions were respectively purified by gel filtration on a Sephadex-G75 column (2.5 cm in diameter × 90 cm). The purification process of the minor fraction is shown in FIG. 9a and that of the main fraction in FIG. 9b. A 10 mM Tris-HCl buffer (pH 8.0) containing 0.15M NaCl and 0.05% NaN$_3$ was used as an eluent, and a flow rate was 10 ml/hr. The main component of PPIase was purified by this purification step to a single component as determined by purity tests on sodium dodecyl sulfate (SDS)-polyacrylamide gel electrophoresis and reversed-phase high performance liquid chromatography. The minor component was further purified using a CM-Sepharose CL-68 column (1.5 cm in diameter × 20 cm) equilibrated with 10 mM sodium acetate buffer (pH 6.0). The elution of PPIase was done by linear gradient of NaCl concentration from 0M 300 ml to 0.25M/300 ml (FIG. 10). The flow rate was 12 ml/hr. By this method, the minor component was purified to a single component as determined by the aforementioned purity tests.

The main component is referred to as PPIase-β. The minor component is referred to as PPIase-α.

EXAMPLE 6

Characterization of *Escherichia coli* PPIase-β

(1) Determination of Molecular Weight

Figure 11:
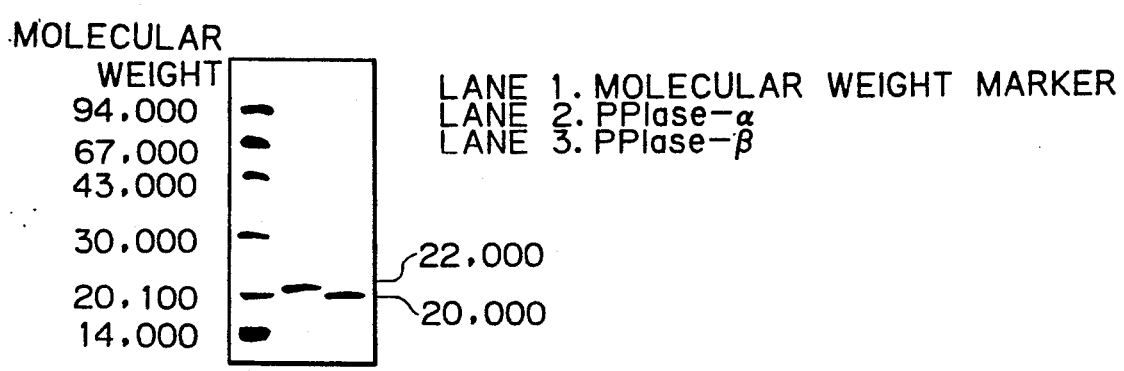
FIG. 11 shows result of determination of molecular weights of purified PPIase-a and PPIase-β.

The molecular weight of the PPIase-β obtained in Example 5 was determined by the SDS-polyacrylamide concentration gradient gel (12%–30% polyacrylamide gel) electrophoresis. As molecular weight standards, phosphorylase (molecular weight: 94,000), bovine serum albumin (67,000), ovalbumin (43,000), carbonic anhydrase (30,000), soybean trypsin inhibitor (20,100), and α-lactalbumin (14,000) were used. The PPIase-α was found to possess a single molecular weight of about 20,000 daltons as shown in FIG. 11.

(2) Determination of the isoelectric point

Figure 12:
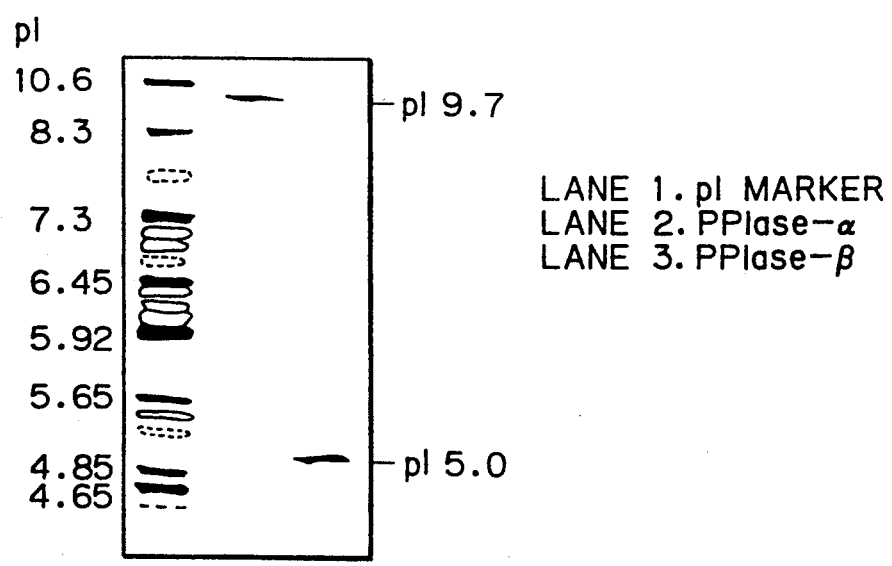
FIG. 12 shows result of determination of isoelectric points of purified PPIase-a and PPXase-β.

The isoelectric point of the PPIase-β obtained in Example 5 was determined by the isoelectric focusing according to Amphline Isoelectric Focusing Manual (LKB Corp), using cytochrome C (pI 10.6), whale myoglobin (8.30), equine myoglobln (7.3), porcine myoglobin (6.45), porcine trifluoroacetyl myoglobin (5.92), azurin (5.65), C-phycocyanine (4.85), and C-phycocyanine (4.65) as standards. The PPIase-β of this invention was found to have a single isoelectric point of about 5.0, as shown in FIG. 12.

(3) Homogeneity in Reverse-phase Colum

Figure 13A:
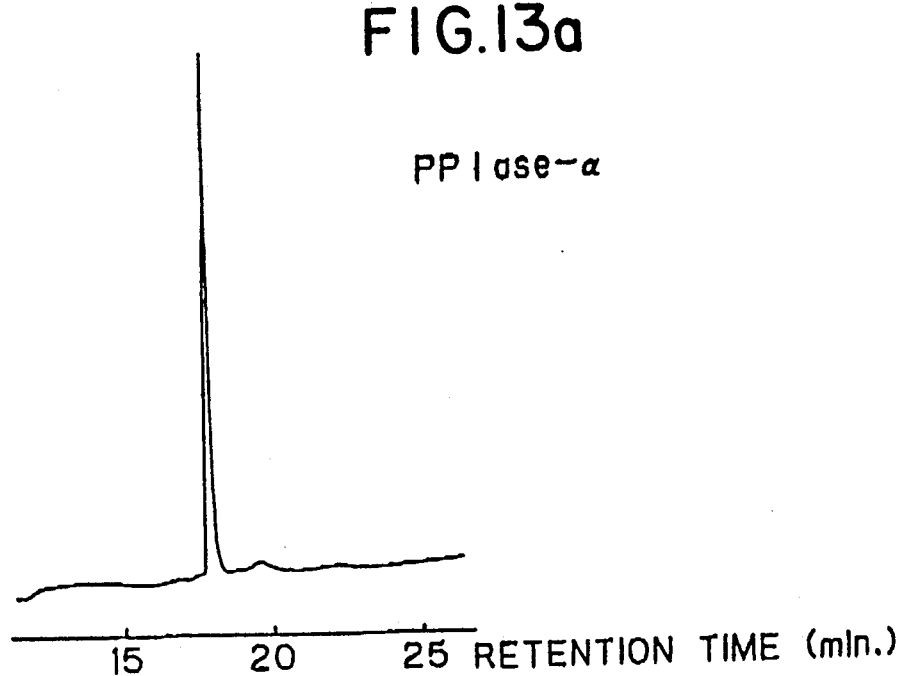
FIG. 13 (a) is a diagram showing that the purified PPIasa-a gives a single peak in analysis with the reverse-phase Aquapore RP-300 column, and FIG. 13 (b) shows results for the purified PPIase-β.
Figure 13B:
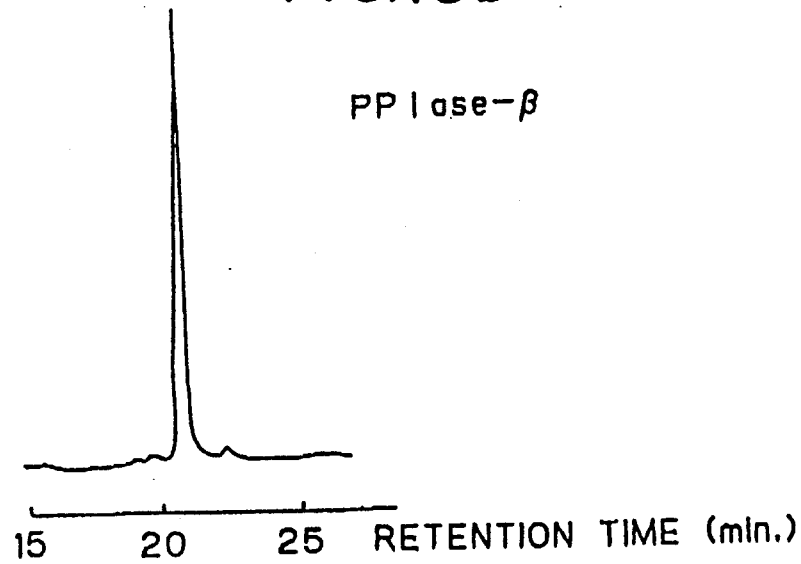

The PPIase-β of the present invention was applied on a reverse-phase Aquapore RP-300 column (2.1 mm in diameter × 3 cm; produced by Applied biosystems Corp), and eluted with 0.1% trifluoroacetic acid containing acetonitrile in a linear gradient concentration of 0% to 100% over a period of 45 minutes at a flow rate of 200 μl/min. The PPIase gave a single peak, as shown in FIG. 13 b.

(4) Determination of Partial Amino Acid Sequence

Amino Acid Sequences of Tryptic Fragments

Figure 14A:
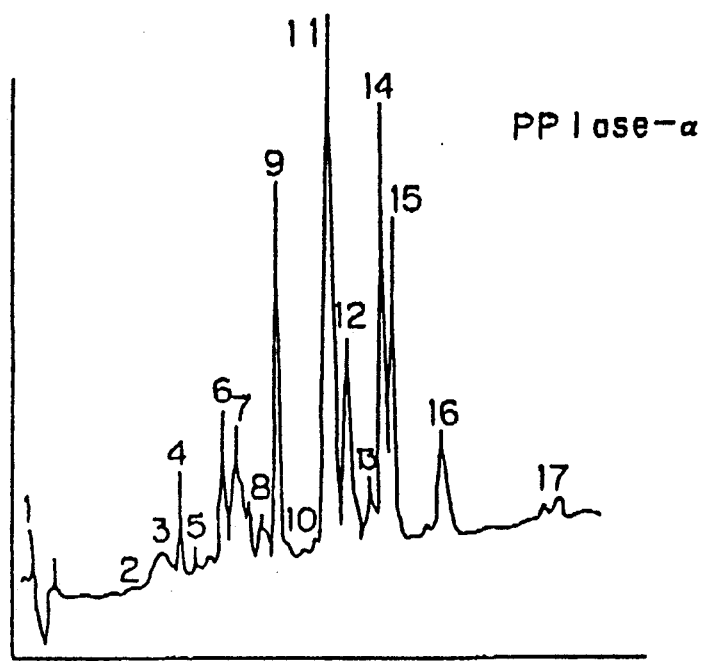
FIG. 14 (a) shows result of separation of peptide fragments obtained from the trypsin digestion of PPIase-α using a reverse-phase Spher 5RP-18 column, and FIG. 14 (B) shows results obtained from the PPIase-β.
Figure 14B:
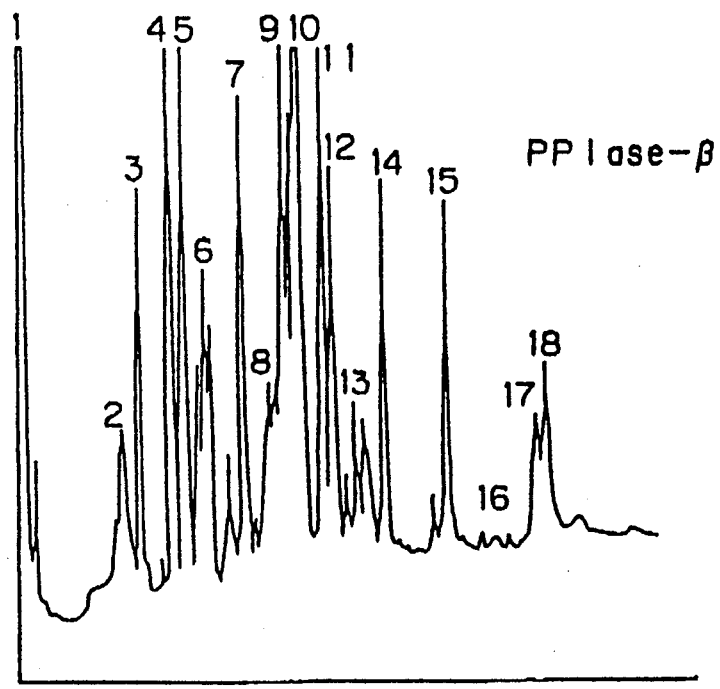

A solution of 200 μg of *E. coli* PPIase-β dissolved in 50 μl of 0.1M of NH$_4$CO$_3$, was digested with 4 μg of TPCk-treated trypsin at 37° C. for 8 hours. The digest was separated and purified on a reversed-phase Spher: 5RP-18 column (2.1 mm in diameter × 3 cm) and Aquapore RP-300 column (2.1 mm in diameter × 3 cm)—(both from Applied Biosystems). In this case, elution was performed with a linear gradient from 0% to 100% of acetonitrile concentration in 0.1% trifluoroacetic acid or 0.1% heptafluorobutyric acid over a period of 45 minutes at a flow rate of 200 μl/min, to obtain 18 peptide peaks. The elution profile is shown in FIG. 14 b.

Seven of the peptide fragments were analyzed to determine the amino acid sequence with an automatic sequencer model 477A (Applied Biosystems) and, as a result, the following amino acid sequences were obtained:

(1) Asn-Phe-Leu-Asp-Tyr-X-Arg
(2) Glu-Gly-Phe-Tyr-Asn-Asn-Thr-Ile-Phe-His-Arg
(3) Val-Ile-Asn-Gly-Phe-Met-Ile-Gin-Gly-Gly-Gly-Phe-Glu-Pro-Gly-Met-Lys
(4) Glu-Pro-Ile-Lys-Asn-Glu-Ala-Asn-Asn-Gly-Leu-Lys
(5) Gly-Thr-Leu-Ala-Met-Ala-Arg
(6) Thr-Gln-Ala-Pro-His-Ser-Ala-Thr-Ala-Gin-Phe-Phe-Ile-Asn-Val-Val-Asp
(7) Ser-Gly-Met-His-Gln-Asp-Val-Pro-Lys-Glu-Asp-Val-Ile-Ile-Glu-Ser-Val-Thr-Val-Ser.

Amino Acid Sequences of Fragments Resulting from Cyanogen Bromide Cleavage

In 70% formic acid, 200 μg of the PPIase was hydrolyzed by treatment with 500 μg of cyanogen bromide overnight. The resultant fragments were separated and purified on reverse-phase Spheri 5RP-18 (2.1 mm in diameter×3 cm) and Aquapore RP-300 (2.1 mm in diameter×3 cm) columns (both from Applied Biosystems). In this case, elution was carried out by a linear gradient of 0% to 100% acetonitrile concentration in 0.1% trifluoroacetic acid or 0.1% heptafluorobutyric acid over a period of 45 minutes as a flow rate of 200 μl/minute to obtain 15 peptide peaks. The elution profile is shown in FIG. 15b.

Six of these peptide fragments were analyzed for amino acid sequencing with an automatic sequencer, model 477A (Applied Biosystems). As the result, the following amino acid sequences were obtained:

(1) Val-Thr-Phe-His-Thr-Asn-His-Gly-Asp-Ile-Val-Ile
(2) Ile-Gln-Gly-Gly-Gly Phe-Glu-Pro-Gly
(3) Lys-Gln-Lye-Ala-Thr-Lys-Glu-Pro-Ile-Lys-Asn-Glu-Ala-Asn-Asn-Gly-Leu-Lys-Asn-Thr-Arg-Gly-X-Leu
(4) Ala-Arg-Thr-Gln-Ala-Pro-His-Ser-Ala-Thr-Ala-Gln-Phe-Phe-Ile-Asn-Val-Val-Asp-Asn-Asp-Phe-Leu-X-Phe-X-Gly
(5) Asp-Glu-Val-Asp-Lys-Ile-Lys-Gly-Val-Ala-Thr-Gly-Arg-Ser-Gly
(6) His-Gln-Asp-Val-Pro-Lys-Glu-Asp-Val-Ile-Ile.

(5) N-terminal Amino Acid Seqcuence

The PPIase-B was analyzed for amino terminal sequence using an amino acid sequencer, model 477A (from Applied Biofystems). As the result, the following sequences were obtained:

Met-Val-Thr-Phe-His-Thr-Asn-His-Gly-Asp-Ile-Val-Ile-Lys-Thr-Phe-Asp-Asp-Lys-Ala-Pro-Glu-Thr-Val-Lys-Asn-Phe-Asp-Tyr.

(6) Amino Acid Composition

To 5 μg of the purified PPIase-β in a test tube was added 0.5 ml of 6N HCl, and the mixture was degassed, sealed in tube, and hydrolyzed at 110° C. for 24 hours. The resultant hydrolyzate was evaporated under a vacuum, and analyzed for amino acid composition using an amino acid analyzer, JLC-300 (Japan Electron Optics Laboratory Co,, Ltd.). The results are shown in Table 2.

TABLE 2

| Amino acid | PPIase-β (Molar ratio) | PPIase-α (Molar ratio) | Recombinant PPIase-β (Molar ratio) |
|---|---|---|---|
| Asp | 22.23 (23)[1] | 26.2 | 22.6 |
| Thr | 11.36 (12) | 10.45 | 11.2 |
| Ser | 5.41 (6) | 7.91 | 5.8 |
| Glu | 18.50 (17) | 17.91 | 16.5 |
| Gly. | 16.00 (16) | 15.80 | 14.2 |
| Ala | 10.00 (10) | 14.43 | 10.0 |
| Cys | — (2) | — | — |
| Val | 11.64 (15)[2] | 14.84 | 13.0 |
| Met | 5.35 (6) | 3.94 | 5.3 |
| Ile | 8.75 (10)[2] | 8.38 | 8.3 |
| Leu | 5.23 (5) | 8.87 | 5.6 |
| Tyr | 3.04 (3) | 4.33 | 2.7 |
| Phe | 11.94 (12) | 11.00 | 11.6 |
| His | 4.98 (5) | 4.59 | 5.0 |
| Lys | 11.33 (11) | 13.85 | 10.7 |
| Arg | 5.00 (5) | 5.52 | 4.9 |
| Pro | 4.04 (5) | 12.35 | 2.6 |
| Trp | — (1) | — | — |

[1]The values in parentheses represent numbers of amino acids obtained from the decided amino acid sequences.
[2]Two Val—Val bonds and three Val-Ile bonds are present in the amino acid sequence.

(7) Sensitivity of *Escherichia coli* PPIase-β to Cyclosporin A (CsA)

Figure 16:
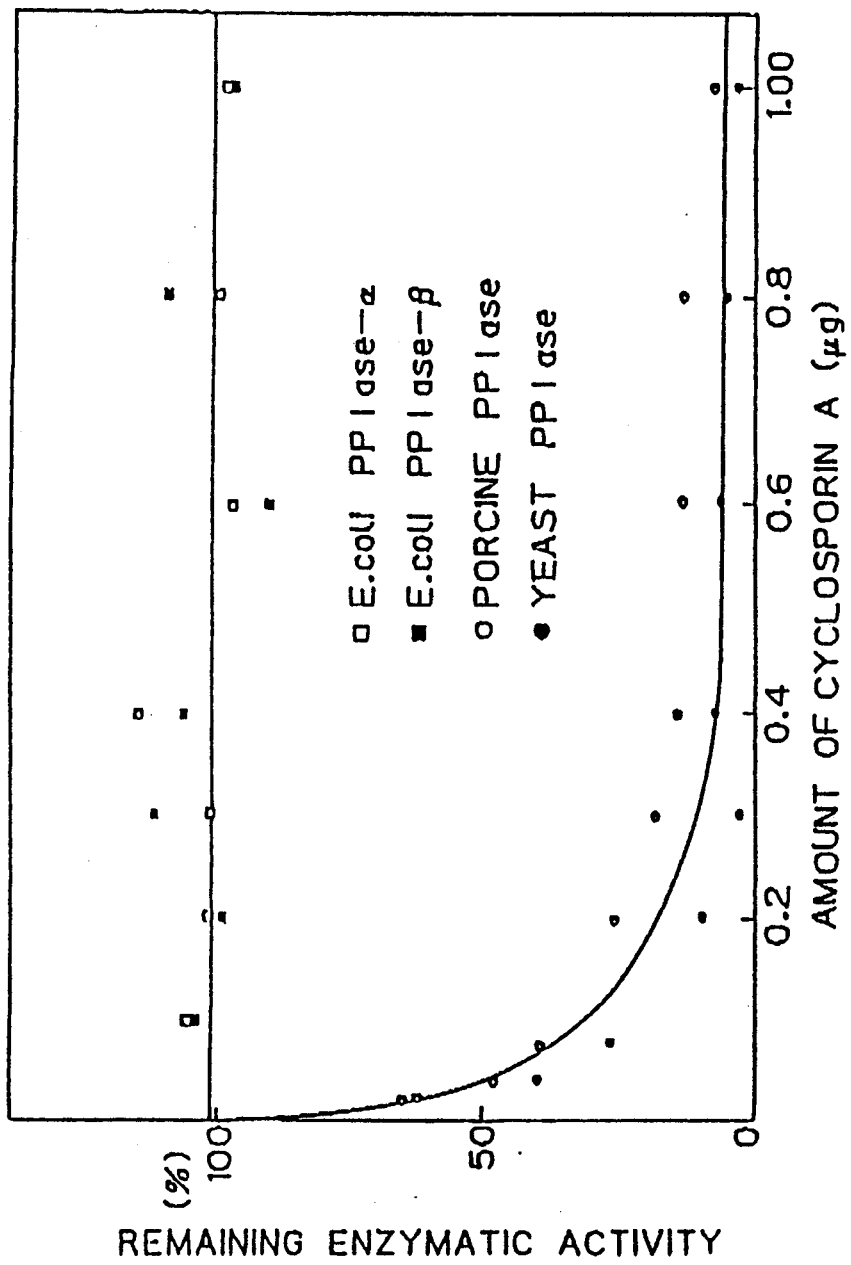
FIG. 16 is a graph showing an effect of CsA on the activities of yeast and E. coli PPIase of the present invention, compared with porcine PPIase activity, is term of the relationship between CsA concentration and residual activity of PPIase.

The inhibition effect of Csa on the activity of purified *E. coli* PPIase-β was determined by the method described in N. Takahashi et al, Nature, 377, 473–475 (1989). The results are shown in FIG. 16. The figure shows the comparison of the degree of inhibition by cyclosporin A on *Escherichia coli* PPIase and the porcine PPIase. The cyclosporin A in a concentration enough to inhibit completely the porcine PPIase and yeast PPIase, brings virtually no inhibition of the *Escherichia coli* PPIase-β. The binding of CsA inhibits porcine PPIase and yeast PPIase activities. Therefore, a positive interrelation appears to exist between the binding activity of CsA to the PPIase and the inhibition effect of CsA of the PPIase activity. It is assumed that the effects of CsA on various organisms, such as antifungal effect, antischistosome effect, antimalarial effect and the like, are manifested through the binding activity of CsA to PPIase, namely the inhibition effect of CsA on PPIase activity. Note, the fact that the inhibition effect of CsA is not observed on *E. coli* PPIase agrees with the fact that the binding activity of CsA present in all of tested eukaryotes was not detected in *E. coli*.

EXAMPLE 7

Characterization of *Escherichia coli* PPIase-α

(1) Determination of Molecular Weight

The molecular weight of *Escherichia coli* PPIase-α was determined following the procedure of Example 6 (1). The results are shown in FIG. 11. *E. coli* PPIase-α found to have a single molecular weight of 22,000 in this figure.

(2) Determination of the Isoelectric Point

The isoelectric point of the *E. coli* PPIase-α was determined following the procedure of Example 6 (2). The results are shown in FIG. 12. PPIase-α is found to possess a single isoelectric point of pI 9.7.

(3) Homogeneity in Reverse-phase Column

In the analysis performed following the procedure of Example 5 (3), E. coli PPIase-α showed a single peak. The results are shown in FIG. 13. Under the given separation conditions, PPIase-α was eluted about 3 minutes earlier than PPIase-β.

(4) Determination of Partial Amino Acid Sequence

Amino Acid Sequences of Tryptic Fragments

In the same manner as used for the PPIase-β, 17 peptide peaks were produced from the PPIase-α. Five of these peptide fragments were analyzed for amino acid sequence using an automatic sequencer, model 477A, and as a result, the following amino acid sequences were obtained:

(1) Ala-Pro-Val-Ser-Val-Gln-Asn-Phe-Val-Asp-Tyr-Val-Asn-Ser-Gly-Phe-Tyr-Asn-Asn-Thr
(2) Thr-Ala-Asp-Lys-Asp-Ser-X-Ala-Asp-Gln-Phe-Phe-Ile-Asn-Val-Ala-Asp-Asn-Ala
(3) X-Met-Asp-Val-Ala-Asp-Lys-Ile-Ser-Gln-Val-Pro
(4) Val-Ile-Pro-Gly-Phe-Met-Ile-Gln-Gly-Gly-Gly-Phe-Thr-Glu
(5) Asp-Phe-Gly-Tyr-Ala-Val-Phe-Gly-Lys.

Amino Acid Sequences of Fragments Cleaved with Cyanogen Bromide

In the same manner as used for the PPIase-β, 10 peptide peaks were obtained from PPIase-α. Four of these peptide fragments were analyzed for their amino acid sequence, and the results are shown below:

(1) Ile-Gln-Gly-Gly-Gly-Phe-Thr-Glu-Gln-(Met)
(2) Ala-Arg-Thr-Ala-Asp-Lys-Asp-Ser-X-Ala
(3) Asp-Val-Ala-Asp-Lys-Ile-Ser-Gln-Val-Pro-X-His-Asp-Val-Gly
(4) Gln-Gln-Lys-Lys-Pro-Asn-Pro-Pro-Ile-Lys-Asn-Glu-Ala-Asp-Asn-Gly-Leu-Arg-Asn-X-Arg-Gly.

(5) N-terminal Amino Acid Sequence

The PPIase-α was analyzed for N-terminal amino acid sequence in the same manner as described in Example 6 (5), and the results are as follows:

Ala-Lys-Gly-Asp-Pro-His-Val-Leu-Leu-Thr-Thr-Ala-Gly-Val-Asn-Ile-Glu-Leu-X-Leu-Asp-Lys-X-Lys.

(6) Amino Acid Composition

The PPIase-α was analyzed for amino acid composition in the same manner as described in Example 6 (6). The results are shown in Table 2.

EXAMPLE 8

Cloning of *Escherichia coli* PPIase-β Gene

High-molecular-weight DNA was prepared from an *E. coli* HB101 strain, according to the method described by Thomas et al. [*J. Mol. Biol*, 11, 476 (1965)]. About 2 μg of the high molecular DNA was digested in 20 μl of a solution [10 mM Tris-HCl (pH 7.5), 100 mM NaCl, 6 mM MgCl$_2$, 6 mM mercaptoethanol, 0.1% gelatin, 10 units of Bgl II (Nippon Gene K.K.), and 10 units of Hind III (Nippon Gene K.K.)] at 37° C. for 3 hours, subjected to 0.8% agarose gel electrophoresis, and transferred onto a membrane filter (Amersham Corp., "Hybond-N") according to the Southern method [Southern, E. M., *J. Mol. Biol.*, 98, 503 (1975)].

The DNA was fixed on the filter by exposure to UV light for 2 minutes and then hybridized with a probe as follows. As the probe, the DNA chain:

5'-ATGAA(AG)CA(AG)AA(AG)GC(TCAG)AC-CAAAGAACC-3', synthesized by an automatic DNA synthesizor (Applied Biosystems Corp., "Motel 380") on the basis of an amino acid sequence from methionine at the 59 position to proline at the 67 position in *E. coli* PPIase-β. The synthetic DNA (20 p moles) was reacted in 50 μl of a solution containing 50 mM Tris-HCl (pH 7.5), 10 mM MgCl$_2$, 5 mM dithiothreitol, 100 μCi [γ-$^{32}$P] ATP (3000 Ci/mmol, from Amersham Corp.), and 12 units of T4 polynucleotide kinase (produced by Takara Shuzo Co., Ltd.) at 37° C. for 60 minutes, to label the 5'-end with $^{32}$P. The filter was immersed in a prehybridization solution [5×Denhardt solution (100×Denhardt solution=2% bovine serum albumin, 2% Ficoll, and 2% polyvinylpyrrolidone), 1 M NaCl, 50 mM Tris-HCl (pH 7.5), 10 mM EDTA (pH 8.0), 0.1% sodium dodecyl sarcosinate, and 20 μg/ml of sonicated salmon sperm DNA] at 37° C. for 1 hour, and then in a hybridization solution [a solution obtained by incorporating in the prehybridization solution about 10$^6$ cpm/ml of the aforementioned labeled DNA] at 37° C. for 15 hours. The filter was washed with a 6×SSC (20×SSC=3M NaCl, 0.3M trisodium citrate) solution at room temperature, further washed with a solution of 3×SSC and 0.1% sodium dodecyl sarcosinate at 37° C. for 30 minutes, and exposed to X-ray film (Kodak, "XAR-5") at −80° C. for 4 days. The developed film showed that about 1 kb of Bgl II/Hind III DNA fragment was hybridized with the probe. Thus, an *E. coli* gene library containing about 1 kb DNA fragments was prepared as follows.

About 50 μg of the aforementioned *E. coli* high-molecular-weight DNA was digested in a solution [10 mM Tris-HCl (pH 7.5), 100 mM NaCl, 6 mM MgCl$_2$, 6 mM mercapto ethanol, 0.1% gelatin, 200 units of a Hind III (Nippon Gene K.K.)], at 37° for 3 hours, and subjected to 0.8% agarose gel electrophoresis. An about 1 kb DNA fragment wa separated and purified by the glass powder method (Bio-101 Corp., "Gene Clean ™").

About 50 ng of the recovered Bgl II/Hind III DNA fragment and about 100 ng of pUC119 vector digested with BamHI and Hind III were ligated in 40 μl of a DNA ligation kit solution A and 8 μl of a solution B (Takara Shuzo Co., Ltd.) at 16° C. for 15 hours, to obtain a recombinant plasmid 20 μl of the resultant reaction mixture was used to transform 400 μl of competent JM 109 strain cells (Epicurian coli ™, STRATAGENE) in accordance with the manufacture's specification. The transformants were spread on ten X-Gal plates with a diameter of 90 mm [50 μg/ml of 5-bromo-4-chloro-3-indolyl-β-D-galactopyranoside, 80 μg/ml of isopropyl-β-D-thiogalactopyranoside, 25 μg/ml of ampicillin, an LB culture medium (1% bacto-trypton, 1% NaCl, 0.5% yeast extract), and 1.5% agar]. These plates were incubated at 37° C. overnight, to obtain about 1,500 transformants as white colonies. They were used as a library for the screening of *E. coli* PPIase genes.

The recombinant colonies were transferred onto a filter (Amersham Corp., "Hybond-N"). The filter was set for 5 minutes on a 3MM filter paper (Whatman Corp.) impregnated with 0.5N NaOH and 1.5M NaCl, with a colony-deposited surface of the filter facing upper side, and then for 5 minutes on the same filter paper impregnated with 1M Tris-HCl (pH 7.5) and 1.5M NaCl. Then, the filter was washed with a 2×SSC solution, air dried, and irradiated with UV light to fix *E. coli* DNA on the filter. The filter thus obtained was subjected to hybridization under the same conditions as described above using a synthetic DNA as a probe. Then, the filter was washed and exposed to X-ray film and developed. Nine positive clones obtained were used for subsequent analysis. Specifically, each of the colonies of interest on the plates was inoculated to an LB culture medium containing 25 μg/ml of ampicillin, and shaken cultured at 37° C. overnight. 1.5 ml of the resultant culture was used to prepare a recombinant DNA by the alkali bacteriolytic method [Ish-Horowicz, D. & J. F. Burke, *Nucleic Acids Res.*, 9, 2989 (1981)]. The 9 clone DNAs thus obtained were subjected to double digestion with EcoRI and Hind III, then to 1% agarose electrophoresis, and further to Southern analysis as described above. As a result, only one clone containing 950 bp of *E. coli* DNA fragment was found to be a positive clone. This plasmid DNA was designated as pEPPIb.

The insert of pEPPIb was subcloned to a M13mp type phage DNA and analyzed by the dideoxy method to determine its nucleotide sequence (FIG. 17). An amino acid sequence estimated from the nucleotide sequence was completely identical with the amino acid sequence of peptide obtained from the *E. coli* main component (PPIase-β); therefore, the isolated gene was established as a gene coding for *E. coli* PPIase-β. This gene coded for a protein consisted of 164 amino acid residues and possessing a molecular weight of 18,184 daltons as calculated from the amino acid sequence. This molecular weight agrees very closely with that estimated from the data of SDS electrophoresis. Moreover, the amino acid composition agrees very closely with the found value (Table 2).

Figure 27A:
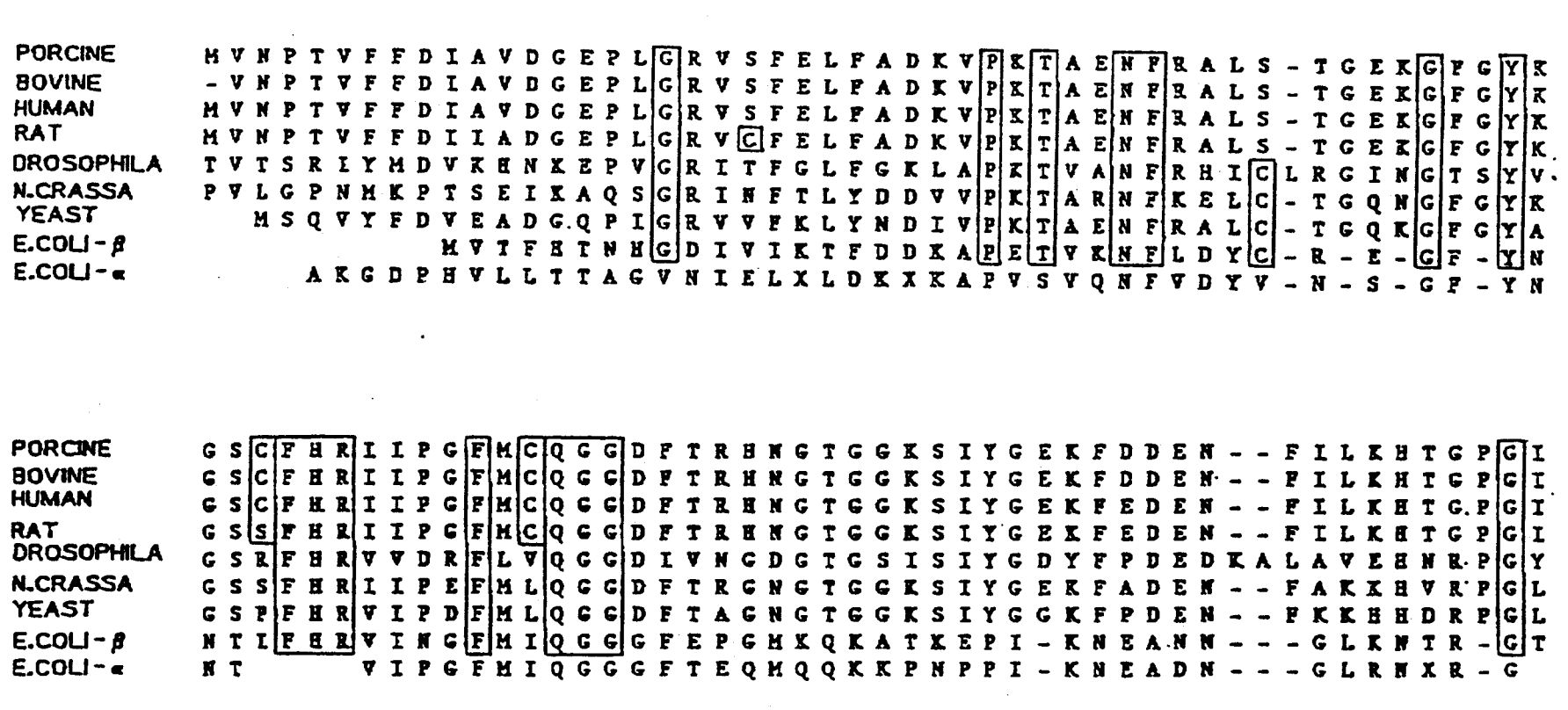

FIG. 27 shows the total amino acid sequence of *E. coli* PPIase-β and partial amino acid sequence of PPIase-α as compared with the sequences of the other cyclophilins. In the figure, amino acids conserved among all species, including *E. coli*, in homologous regions are within boxes. The amino acid sequence of *E. coli* PPIase-β shows about 25% of homology to those of cyclophilin/PPIases from the other species, and especially high homology in regions from the 30th to 70th residues and from the 100th to 120th residues as counted from the amino terminal side was observed. Also *E. coli* PPIase-α shows a partially high homology to PPIase-β and conserved amino acid residues in highly homologous regions among the sequences of the other species. Therefore, both of PPIase-β and -α from *E. coli* appear to be cyclophilin-like PPIases. Unlike the cyclophilin/PPIases from the other species, specifically eukaryotes the PPIases from *E. coli* possess no sensitivity to CsA. The comparison of their structures is believed to offer the basis for the elucidation of the CsA binding pattern of other species, and of the mechanism of action of PPIases as enzyme, and the like.

In the case of porcine PPIase, an SH modifying reagent induces modification of four cysteine residues and deprives its enzymatic activity. However, the modification of one of cysteine is inhibited, when CsA binds to the enzyme. After this modification, the enzymatic activity is recovered by releasing CsA from the enzyme by dilution. It has been considered, therefore, that CsA protects the cysteine residue from the modification with the SH reagent by directly interacting with the cysteine residue as active group [Fisher, G., Wittmann-Liebold, B., Lang, K., Kekfhaber, T. & Schmid, F. X. *Nature* 337, 476–478 (1989)]. On the other hand, the PPIases derived from *E. coli* have affected on their enzymatic activity neither by the CsA nor by the SH modifying reagent.

Looking at the amino acid sequences in FIG. 27 from this point of view, no cysteine residue is found to be perfectly conserved among all of PPIases from the given organisms.

Figure 28:
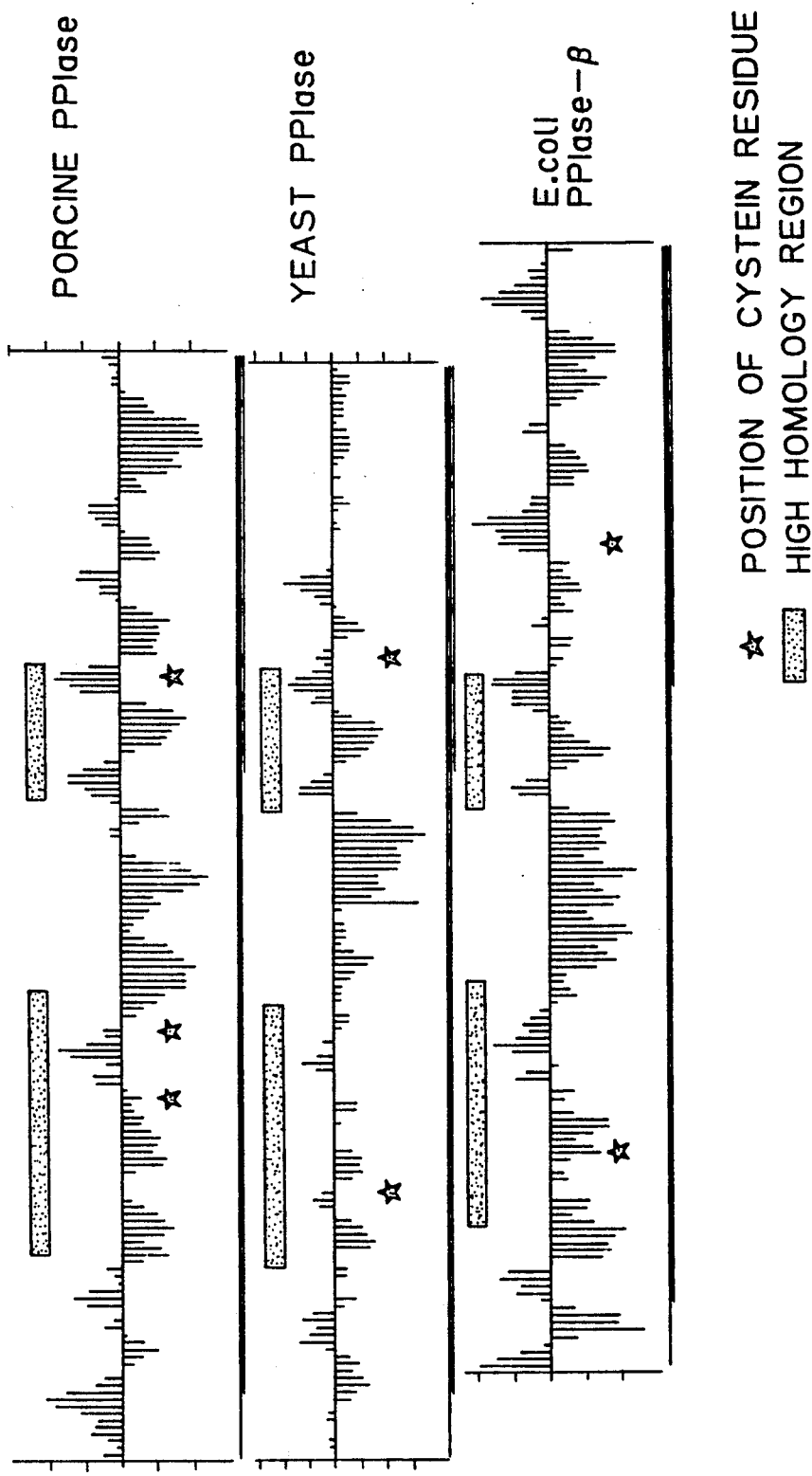

In the comparison of hydropathy patterns [Kyte, J. M. & Doolittle, R. F., *J. Mol. Biol.* 157, 105–132 (1982)] of porcine and yeast PPIases demonstrated to bind CsA and to be inhibited by CsA on the enzymatic activities (see our previous patent application related to yeast PPIase) with *E. coli* PPIase-β demonstrated to be not inhibited by CsA, Cys-115 in porcine and Cys-117 in yeast which are common to both porcine and yeast PPIases sensitive to CsA and absent from *E. coli*, are located at similar positions on hydropathy patterns (FIG. 28).

No cysteine residues are present at such positions in *E. coli* PPIase-β and, therefore, Cys-115 in porcine and Cys-117 in yeast are predicted to interact directly with CsA. In the light of the data for *E. coli*, the theory that the above cysteine residues are active groups directly associated with the expression of enzymatic activity leaves room for doubt. At least in the case of *E. coli*, no proof has been offered that the cysteine residues are active groups. Rather, the two high homology regions found among the amino acid sequences from all species, are believed to be important for the expression of the activities.

Note, *Escherichia coli* HB101/pEPPIb containing plasmid pEPPIb has been deposited at the Fermentation Research Institute, Agency of Industrial Science and Technology under FERM P-11042.

EXAMPLE 9

Construction of Plasmid pBLEPPIb (FIG. 18)

In 100 μl of a solution [50 mM Tris-HCl (pH 7.6), 7 mM MgCl$_2$, 150 mM KCl, and 20 units of PvuI (produced by Nippon Gene K.K.)], 6 μg of a plasmid (pEPPIb) containing *E. coli* PPIase-β gene was digested at 37° C. for 180 minutes. The digest was extracted twice with 50 μl of a phenol/chloroform (1:1) mixture to remove proteins, and precipitated with ethanol. The recovered DNA was dried with a centrifugal evaporator, dissolved in 100 μl of a Mung bean nuclease buffer (Takara Shuzo Co. Ltd., "DNA deletion kit"). After an addition of 2 μl of Mung bean nuclease (Takara Shuzo Co., Ltd., "DNA deletion kit"), the mixture was allowed to react at 37° C. for 60 minutes, extracted twice with 50 μl of a phenol/chloroform (1:1) mixture to remove proteins, and precipitated with ethanol. The recovered DNA was dried with a centrifugal evaporator, reacted with 30 μl of a solution [100 mM Tris-HCl (pH 7.6), 7 mM MgCl$_2$, 50 mM NaCl, and 20 units of EcoRI (Nippon Gene K.K.)] at 37° C. for 60 minutes, and subjected to 1.2% agarose gel electrophoresis. The inserted DNA was recovered by the glass powder method (Bio-101 Corp., "Gene Clean ™"), and extracted with 10 μl of a TE solution [10 mM Tris-HCl (pH 7.5) and 1 mM EDTA].

4 μl of the inserted DNA was ligated with about 15 ng of a vector DNA (Bluescript II SK+) previously digested with the restriction enzymes, EcoRI (produced by Nippon Gene K.K.), and EcoRV (produced by Nippon Gene K.K.), in 30 μl of DNA Ligation kit solution A (Takara Shuzo Co., Ltd.) and 5.5 μl of solution B at 16° C. for 16 hours, to obtain a recombinant plasmid.

*Escherichia coli* XL-1 Blue was transformed with 20 μl of the ligation mixture by the calcium chloride method [Mandel, M & Higa, A. J. Mol. Biol., 53, 149 (1970)]. The transformant was selected as white colonies obtained by culturing the cells on an X-Gal plate (155 μg/ml 5-bromo-4-chloro-3-indolyl-β-D-galactopyranoside, 80 μ/ml isopropyl-β-D-thiogalactopyranoside, 50 μg/ml ampicillin, 1% NaCl, 0.5% yeast extract, 1% trypton, and 1.5% agar) at 37° C. for 16 hours.

The transformant was inoculated to an LB culture medium (1% NaCl, 0.5% yeast extract, and 1% trypton) containing 50 μg/ml of ampicillin, and cultured therein at 37° C. for 6 hours. From the culture, a plasmid DNA was prepared by the alkali bactertiolytic method [Birnboim, H. C. & Doly. J. (1979) *Nucleic Acids Res.* 7, 1513], dissolved in 30 μl of a TE solution. One third of the DNA thus obtained was treated with a solution [50 mM Tris-HCl (pH 7.6), 7 mM MgCl$_2$, 100 mM NaCl, 25 ng/μl ribonuclease A, 5 units of Xho I (Takara Shuzo Co., Ltd.), and 5 units of Bam HI (Nippon Gene K.K.)] at 37° C. for 60 minutes, and then subjecting to 0.8% agarose gel electrophoresis, to confirm a plasmid containing the desired insert. The transformant was cultured in 200 ml of an LB medium containing 50 μg/ml of ampicillin and subjected to the alkali bacteriolytic method, to prepare a plasmid DNA. The plasmid DNA was further purified by cesium chloride density gradient centrifugation [Maniatis, T. et al. (1982) *Molecular Cloning: A Laboratory Manual*, Cold Spring Habor Laboratory. This plasmid was designated as pBLEPPIb.

EXAMPLE 10

Figures 1, 19:
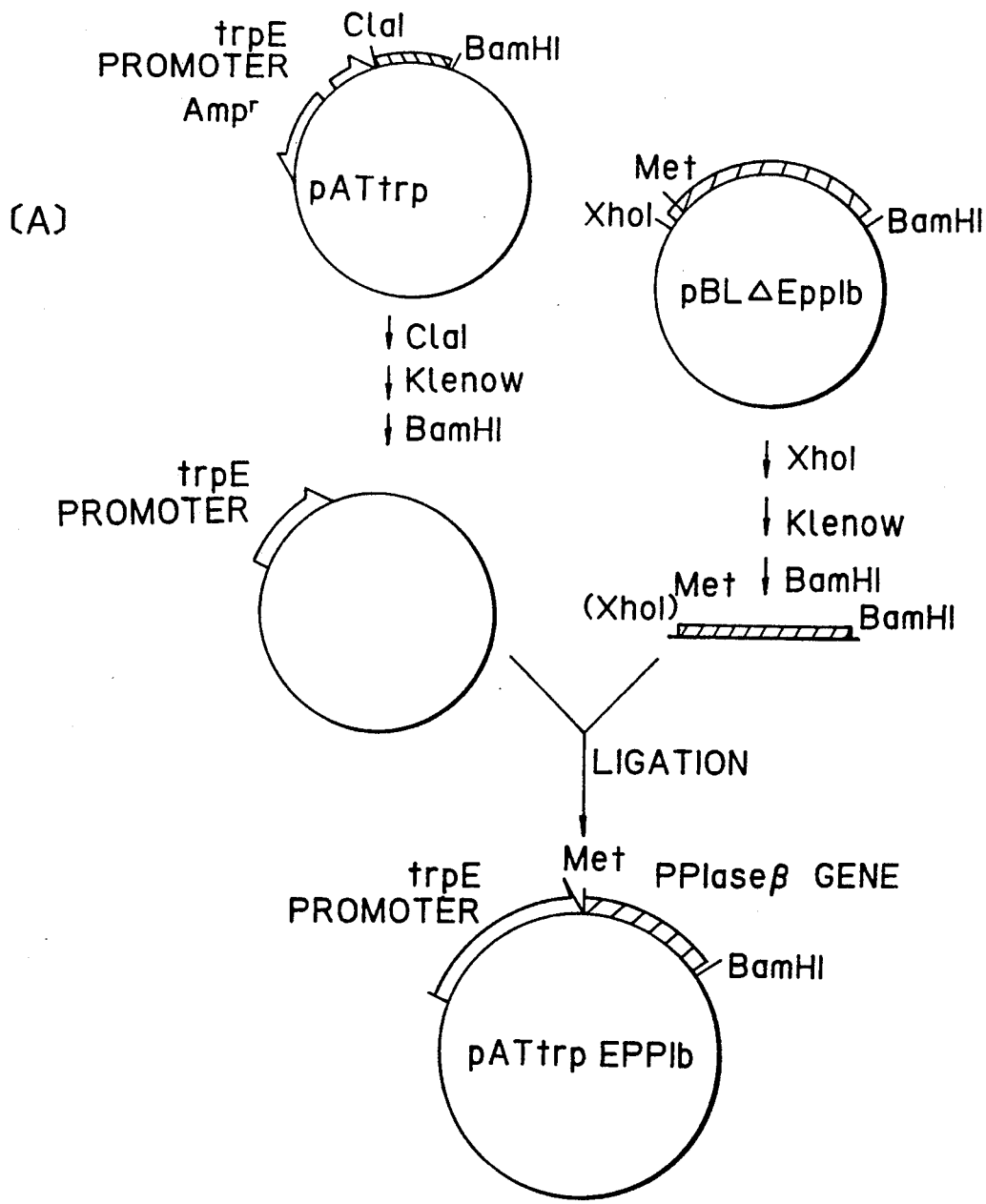

Construction of Plasmid pBLΔEPPIb (FIG. 19)

29 μg of PBLEPPIb was digested in 1 ml of a solution [50 mM Tris-HCl (pH 7.6), 7 mM MgCl$_2$, 150 mM NaCl and 200 units of Sal I] at 37° C. for 12 hours, and then left to stand at 5° C. for 45 minutes to inactivate the restriction enzymes. To 500 μl of the resultant solution were added 10 μl of 1 mM Thio-dNTP (Stratogene Corp.; EXO/MUNG deletion kit) and 10 μl of Klenow fragment (Takara Shuzo Co., Ltd.), the mixture was allowed to react at 37° C. for 45 minutes, to blunt the cleavage sites. The DNA solution was extracted with a phenol/chloroform (1:1) mixture to remove proteins, and precipitated with ethanol to recover the DNA. Next, this DNA was digested in 25 μl of a solution [50 mM Tris-HCl (pH 7.6), 7 mM MgCl$_2$, 60 mM NaCl, and 40 units of Hind III], phenol extracted, ethanol precipitated, and dried by centrifugal evaporator.

The DNA thus obtained was dissolved in 100 μl of an Exo III buffer (Takara Shuzo Co., Ltd.; DNA deletion kit), reacted with 1 μl of exonuclease III (the same kit) at 23° C. In the course of this reaction, 10 μl of sample were taken up at intervals of 20 seconds, mixed with 10 μl of Mung mean nuclease buffer, and placed on ice to stop the reaction. A total of ten samples thus obtained were combined, heated at 65° C. for 5 minutes to inactivate exonuclease III, and then treated with 2 μl of Mung bean nuclease (produced by the same manufacturer) at 37° C. for 60 minutes to create a DNA deletion.

The mixture was phenol extracted and ethanol precipitated to recover the DNA. One quarter of the DNA thus recovered was treated with 100 μl of DNA Ligation kit solution A and 12 μl of solution B (both from Takara Shuzo Co., Ltd.) as 16° C. for 120 minutes, to cyclize the DNA.

The cyclized DNA was digested with Sal I to remove unreacted plasmid DNA. The obtained plasmid DNA was used to transform the *E. coli* XL-1 Blue strain by the CaCl$_2$ method. A plasmid DNA was purified in the same manner as described above from the transformant, double digested with Xho I (Takasa Shuzo Co., Ltd.) and EcoRI Nippon Gene K.K.), and then subjected to 1.2% agarose gel electrophoresis, to select a transformant having an insert with a desired length. The 5'-terminal base sequence of the PPIase-β gene in plasmid DNA molecule from the transformant was determined by using a M13 Sequencing kit (Toyobo K.K.). One clone believed to be most suitable for the construction of the PPIase-β gene expressing plasmid, was selected. This plasmid was designated as pBΔEPPIb.

EXAMPLE 11

Constructton of Expression Plasmid pATtrp EPPIb

Ten μg of the pBLΔEPPIb plasmid DNA obtained in Example 10 was treated with 50 μl of a solution [50 mM Tris-HCl (pH 7.6), 7 mM MgCl$_2$, 100 mM NaCl, and 20 units of Xho I (Takara Shuzo Co., Ltd.)] at 37° C. for 120 minutes, phenol extracted, and ethanol precipitated to recover the DNA. This DNA was treated wlth 50 μl of Klenow buffer [7 mM Tris-HCl (ph 7.5), 7 mM MgCl$_2$, 100 mM NaCl, O.1 mM EDTA, and 5 Units of Klenow fragment (Takara Shuzo Co., Ltd.)] at 37° C. for 50 minutes, to blunt the Xho I cleavage sites, phenol extracted, and then ethanol precipitated to recover the DNA. The DNA thus obtained was further treated with 30 μl of a solution [50 mM Tris-HCl (pH 7.6), 7 mM MgCl$_2$, 100 mM NaCl, and 20 units of BamH I (Nippon Gene K.K.)] at 37° C. for 60 minutes, subjected to 1.2% agarose gel electrophoresis, and the inserted DNA was recovered by the glass powder method. The inserted DNA was extracted from 10 μl of a TE solution.

On the other hand, Pst I/Cla I double-digested pP$_L$-TNF (Ikenaka et al., *Chem. Pharm. Bulletin*, in press) comprising a trp promotor trp LSD sequence, was ligated with a Pst I/Cla I large fragment from pAT153, to obtain pATtrp vector (disclosed in Japanese patent application no. 88-37,452) and 10 μg of the vector DNA was digested with Cla I (BioRad Co.), blunted the cleavage site with a Klenow fragment digested with a BamH I, and then subjected to 1.2% agarose gel electrophoresis to separate the inserted DNA. The inserted DNA was recovered by the glass powder method, and extracted from 10 μl of TE solution.

Then, 2 μl of the DNA fragment containing *E. coli* PPIase-β gene obtained was ligated with 30 μl of a linearized pATtrp in 30 μl of a DNA Ligation kit solution A and 6 μl of solution B (both from Takara Shuzo Co., Ltd.) at 16° C. for 16 hours, a cyclic recombinant plasmid was obtained. The expression plasmid was designated as pATtrp EPPIb. *Escherichia coli* HB 101 strain was transformed with using the expression plasmid pATrp EPPIb by the calcium chloride method.

Figure 20:
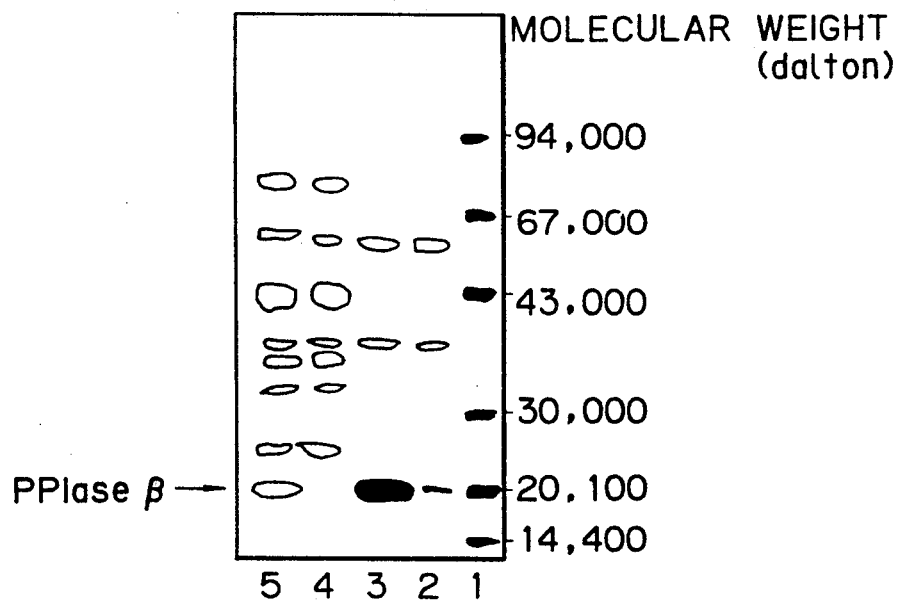
FIG. 20 shows an expression profile of the PPIase produced-β produced by transformed E. coli cells.

The obtained transformant was used for an experimental expression of *E. coli* PPIase-β in *E. coli* cells. Is the following experiment, the transformant containing pATtrp plasmid was used as a control. Fifty μl of a glycerol stock of the transformant was inoculated to 5 ml of an LB culture medium containing 50 μg/ml of ampicillin, and cultured at 37° C. overnight. Fifty μl Of the preculture was inoculated to 100 ml of a M9CA-amp culture medium (0.05% NaCl, 0.6% Na₂HPO₄, 0.3% KH₂PO₄, 0.1% NH₄Cl, 0.2% casamino acid, 2 mM MgSO₄, 0.2% glucose, 0.1 mM CaCl₂, 50 μg/ml ampicillin, pH 7.4) and shaken, cultured at 37° C. When the turbidity (absorbance at 600 nm) of culture reached about 0.3, 3-β-indol-acrylic acid (IAA) was added to a final concentration of 50 μg/ml to induce expression, and the shaken culture was further continued as 37° C. for about 20 hours. It was confirmed that the production of PPIase-β by the transformant was above 50 times more than that of the control, on quantitative determination by densitometry following electrophoresis (FIG. 20). It is clear that the PPIase-β is expressed in a large amount in the soluble fraction of the transformant.

EXAMPLE 12

Production of PPIase-β

To 5 ml of an LB-Am culture medium (10 g/l bactotrypton, 5 g/l yeast extract, 5 g/l NaCl, and 50 μg/ml ampicillin) was inoculated 50 μl of the aforementioned transformant glycerol stock, and cultured at 37° C. overnight. To 50 ml of an LB-Amp culture medium was inoculated 0.5 ml of the resultant culture and cultured again overnight. Then, 4 ml of the culture was inoculated to 400 ml of M9CA-Amp culture medium, cultured at 37° C. for 2 hours, and after adding 0.8 ml of 20 mg/ml of 3-β-indolacrylic acid (IAA) solution, cultured further for 24 hours.

The culture in 400 ml of M9CA-Amp medium was carried out in 10 replications. About 4 liters of combined culture was centrifuged at 6,000 rpm for 5 minutes at 4° C. to obtain 11.8 g of wet bacterial cells.

Figure 21:
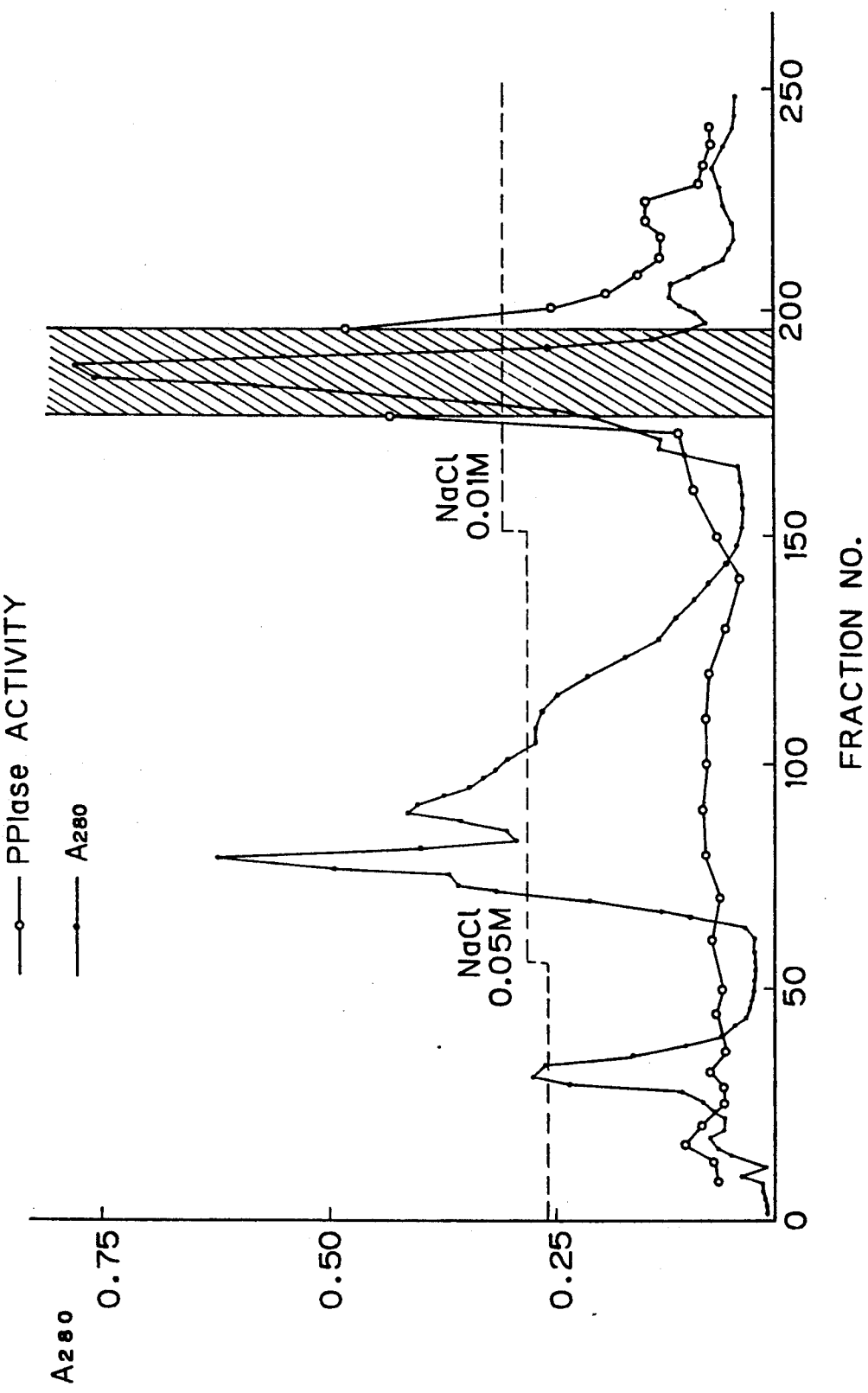
FIG. 21 Shows an elution profile in separation of PPIase-β produced by the transformed E. coli cells using a DEAE-Sepharose CL-6B column.
Figure 22:
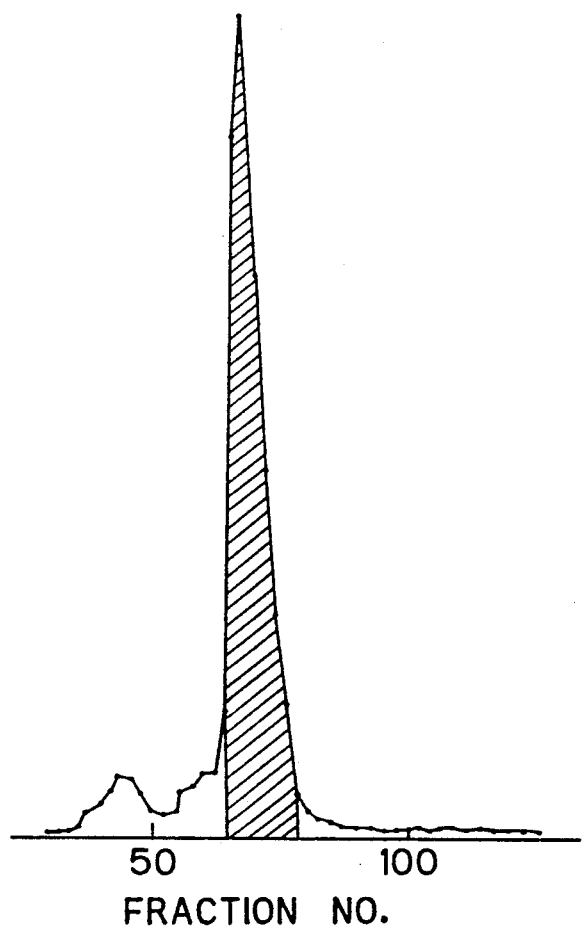
FIG. 22 shows an elution profile in purification by gel filtration of a fraction obtained in FIG. 21 on a Sephadex-675 column.

11.8 g of the bacterial cells were suspended in 50 ml of 0.1M Tris-HCl (ph 7.5) solution containing 5 mM 2-mercaptoethanol, and treated with 11.8 mg of lysozyme at 30° C. for 1 hour. The mixture was sonicated for 1 minute to homogenize the cells, and centrifuged at 18,000 rpm for 30 minutes. This supernatant was dialyzed three times against 3 liters of 10 mM Tris-HCl solution (pH 8.0) containing 0.05% NaN₃, and then applied on a DEAE-Sepharose CL-6B (2.5 cm in diameter×40 cm) column previously equilibrated with the same buffer. The enzymatic activity of the peptidyl prolyl cis-trans isomerase was measured by the method described in Takahashi, N., et al, Nature, 337, 473–475 (1989). The elution of the protein from the column was effected by stepwise elution of 0.05M, 0.1M, 0.2M, and 0.3M NaCl. The desired enzyme was detected in an eluate having a salt concentration of 0.1M (FIG. 21). Fractions 176–196 having an enzymatic activity was concentrated with 80% saturated ammonium sulfate, and separated on a Sephadex-G75 column (2.5 cm in diameter×90 cm) with 10 mM Tris-HCl (pH 8.02) containing 0.15M NaCl and 0.05% NaN₃ (FIG. 22), to obtain a purified sample. The fractions 64–78 shown in the figure were combined as a purified fraction, and characterized as described below.

EXAMPLE 13

Characteristic Comparison of Between Recombinant Escherichia coli PPIase-β and Natural Countertype

(1) Determination of Molecular Weight

Figure 23:
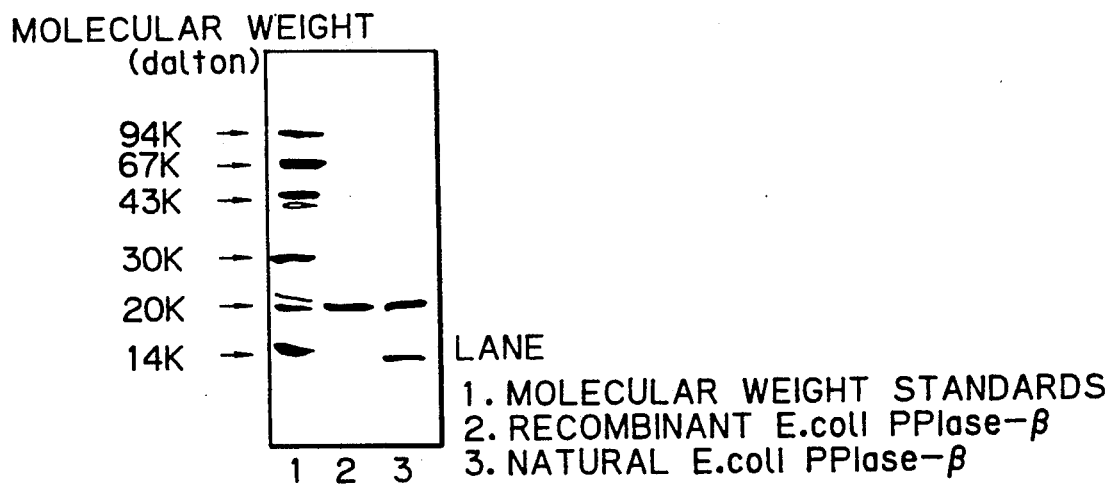
FIG. 23 shows the comparison between a natural PPIase-β and recombinant PPIase (β) in SDS-electrophoresis.

The molecular weights were determined by sodium dodecyl sulfate-polyacrylamide gradient gel (12% to 30% polyacrylamide gel) electrophoresis. As molecular weight standards, phosphorylase b (molecular weight; 94,000), bovine serum albumin (67,000), ovalbumin (43,000), carbonic anhydrase (30,000), soybean trypsin inhibitor (20,100), and α-lactalbumin (14,400) were used. The recombinant E. coli PPIase-β was found to possess a single molecular weight of 20,000 daltons as shown in FIG. 23, which could not be discriminated from that of natural countertype.

(2) Determination of Isoelectric Point

Figure 24:
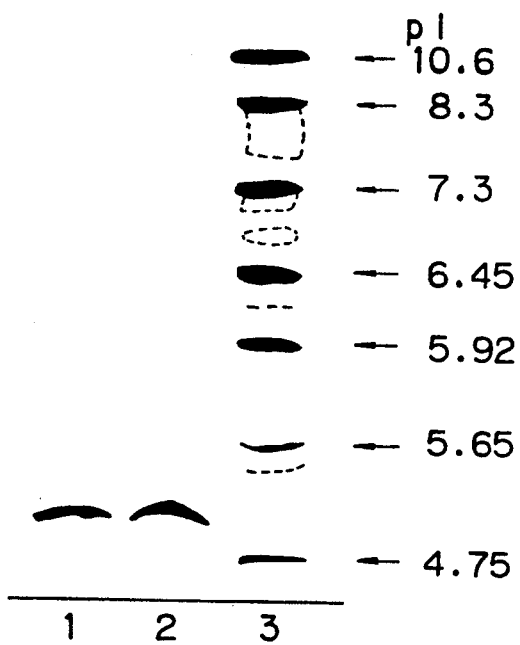
FIG. 24 shows the comparison between a natural PPIase-β and recombinant PPIase (β) of their isoelectric points by the isoelectric focusing.

The isoelectric points were determined according to the Ampholline Isoelectric Focusing Manual published by LKB Corp. As standards, cytochrome C (pI 10.6), whale myoglobin (8.3), equine myoglobin (7.4), porcine myoglobin (6.45), porcine trifluoroacetyl myoglobin (5.92), azurin (5.65), and C-phycocyanine (4.85, 4.65) were used. The results are shown in FIG. 24. The recombinant E. coli PPIase-β was found to possess a single isoelectric point of about 6.2 as shown in the figure, which could not be discriminated from the natural countertype.

(3) Comparison by Reversed-phase Column Chromatography

The sample was applied an a reversed-phase-Aquapore RP-300 column (2.1 mm in diameter×3 cm; Applied Biosystems Corp.). Elution was performed by a linear gradient of 0% to 100% acetonitrile concentration in 0.1% trifluoroacetic acid over a period of 45 minutes at a flow rate of 200 μl/minute. The purified enzyme gave a single peak. The retention time of the recombinant sample of the columns could not be discriminated from that of natural enzyme. The recombinant sample and the natural sample were mixed and subjected to separation. The mixture gave a single peak and failed to show any difference in behavior on the reversed-phase column (FIG. 25).

(4) Amino Terminal Sequence

When the standard PPIase obtained an Example 7 was analyzed with an automatic protein sequencer, Model 477A (produced by Applied Biosystems), the following sequence from the amino terminal methionine to the 20th residue was entirely identical with that of the natural enzyme:

```
1                                          10
Met—Val—Thr—Phe—His—Thr—Asn—His—Gly—Asp—Ile
                                           20
Val—Ile—Lys—Thr—Phe—Asp—Asp—Lys—Ala.
```

(5) Amino Acid Composition

In a test tube, 20 μg of the purified PPIase was mixed with 0.5 ml of 6N HCl, degassed, sealed, and hydrolyzed at 110° C. for 24 hours. The resultant hydrolyzate was dried under a vacuum, and then analyzed for amino acid composition with an amino acid analyzer, Model JLC-300 (NIPPON DENSI Co., Ltd.). The results are shown in Table 2. This table gives the composition values of recombinant and natural enzymes, indicating close agreement.

(6) Determination of the Specific Activity of Enzyme

Figure 26:
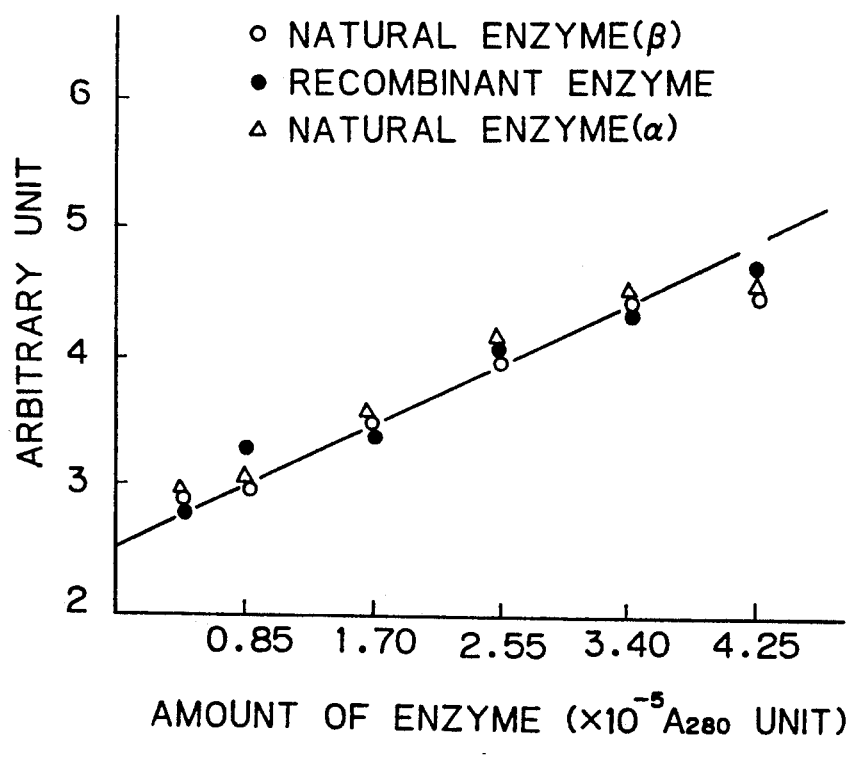
FIG. 26 shows the comparison among natural PPIase-α, natural PPIase-(β), and the recombinant PPIase-β for their activities.

The specific activities of the recombinant and natural enzymes were calculated on the basis of the values obtained from the activity measurement according to the method described in N. Takahashi et al, *Nature*, 377, 473-475 (1989). As a result, the specific activity of the natural enzyme was 51,480 arbitrary units/$A_{200}$ 1 unit, while that of the recombinant enzyme was 52,876 arbitrary units/$A_{280}$ 1 unit. Thus, no distinction could be made on specific activity (FIG. 26).

Deposition of Microorganisms

*Escherichia coli* JM107/pUC-y-PPI containing plasmid pUC-y-PPI has been deposited at the Fermentation Research Institute, Agency of Industrial Science and Technology (FRI), 1-3 Higashi 1-chome, Tsukuba-shi, Ibaraki, 305 Japan, as FERM P-10812 on Jul. 4, 1989, and transferred to an international deposition under the Budapest treaty, as FERM BP-3002, on Jul. 11, 1990.

*Escherichia coli* HB101/pEPPIb containing plasmid pEPPIb has been deposited at the FRI as FERM P-11042 on Oct. 3, 1989, and transferred to an international deposition under the Budapest treaty as FERM BP-3003 on Jul. 11, 1990.

We claim:

1. An isolated and purified *Escherichia coli* peptidyl prolyl cis-trans isomerase $\beta$ possessing the characteristics:
   (1) acting on and isomerizing an $X_{aa}$—Pro bond (wherein $X_{aa}$ stands for any amino acid and Pro for L-proline) in a peptide chain,
   (2) exhibiting a single molecular weight of about 20,000 daltons on sodium dodecyl sulfate-polyacrylamide concentration gradient gel electrophoresis,
   (3) exhibiting a single isoelectric point of about 5.0 on isoelectric focusing, and
   (4) not being inhibited by CsA.

2. The enzyme $\beta$ according to claim 1, which possesses the following amino acid sequence:

Met Val Thr Phe His Thr Asn His Gly Asp
Ile Val Ile Lys Thr Phe Asp Asp Lys Ala
Pro Glu Thr Val Lys Asn Phe Leu Asp Tyr
Cys Arg Glu Gly Phe Tyr Asn Asn Thr Ile
Phe His Arg Val Ile Asn Gly Phe Met Ile
Gln Gly Gly Gly Phe Glu Pro Gly Met Lys
Gln Lys Ala Thr Lys Glu Pro Ile Lys Asn
Glu Ala Asn Asn Gly Leu Lys Asn Thr Arg
Gly Thr Leu Ala Met Ala Arg Thr Gln Ala
Pro His Ser Ala Thr Ala Gln Phe Phe Ile
Asn Val Val Asp Asn Asp Phe Leu Asn Phe
Ser Gly Glu Ser Leu Gln Gly Trp Gly Tyr
Cys Val Phe Ala Glu Val Val Asp Gly Met
Asp Glu Val Asp Lys Ile Lys Gly Val Ala
Thr Gly Arg Ser Gly Met His Gln Asp Val
Pro Lys Glu Asp Val Ile Ile Glu Ser Val
Thr Val Ser Glu.

3. A method for producing of an *Escherichia coli* peptidyl-prolyl cis-trans isomerase $\beta$, comprising recovering the enzyme of claim 1 from cells of *Escherichia coli*.

4. An isolated and purified *Escherichia coli* peptidyl-prolyl-cis-trans isomerase $\alpha$ possessing the characteristics:
   (1) acting on and isomerizing an $X_{aa}$—Pro bond (wherein $X_{aa}$ stands for any amino acid and Pro for L-proline) in a peptide chain,
   (2) exhibiting a single molecular weight of about 22,000 daltons on the sodium dodecyl sulfate-polyacrylamide concentration gradient gel electrophoresis,
   (3) exhibiting a single isoelectric point of about 9.7 on the isoelectric focusing, and
   (4) not being inhibited by CsA.

5. An *Escherichia coli* peptidyl-prolyl cis-trans isomerase $\alpha$ according to claim 4, which possesses the following partial amino acid sequence:
   Ala-Lys-Gly-Asp-Pro-His-Val-Leu-Leu-Thr-Thr-Ala-Gly-Val-Asn-Ile-Glu-Leu-X-Leu-Asp-Lys-X-Lys.

6. A method of producing an *Escherichia coli* peptidyl-prolyl cis-trans isomerase $\alpha$, comprising recovering an enzyme of claim 4 from cells of *Escherichia coli*.

* * * * *